US012577537B2

(12) United States Patent
Lu et al.

(10) Patent No.: US 12,577,537 B2
(45) Date of Patent: Mar. 17, 2026

(54) METHOD FOR CULTURING PRIMARY CANCER CELLS THROUGH SIMULATED MICROGRAVITY-INDUCED REPROGRAMMING AND APPLICATIONS THEREOF

(71) Applicant: SHANDONG UNIVERSITY, Jinan (CN)

(72) Inventors: Haiquan Lu, Jinan (CN); Jia Liu, Jinan (CN); Guangyu Ji, Jinan (CN); Zhaoxue Yu, Jinan (CN); Ziliang Nie, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 19/181,736

(22) Filed: Apr. 17, 2025

(65) Prior Publication Data

US 2025/0368964 A1     Dec. 4, 2025

(30) Foreign Application Priority Data

May 30, 2024   (CN) .......................... 202410683594.4
May 30, 2024   (CN) .......................... 202410683596.3

(51) Int. Cl.
*C12N 5/09*          (2010.01)

(52) U.S. Cl.
CPC ........ *C12N 5/0693* (2013.01); *C12N 2503/02* (2013.01); *C12N 2509/00* (2013.01); *C12N 2513/00* (2013.01); *C12N 2525/00* (2013.01)

(58) Field of Classification Search
None
See application file for complete search history.

(56) References Cited

U.S. PATENT DOCUMENTS

2010/0062435 A1     3/2010   Claudio et al.

FOREIGN PATENT DOCUMENTS

| CN | 101508973 A | 8/2009 | | |
| CN | 101833611 A | 9/2010 | | |
| CN | 102787092 B | * 1/2018 | ........... | C12N 5/0625 |
| CN | 108913662 A | 11/2018 | | |
| CN | 110643672 A | 1/2020 | | |
| CN | 113403278 A | 9/2021 | | |
| CN | 109355261 B | 12/2021 | | |
| CN | 114304066 A | 4/2022 | | |
| CN | 115261325 A | 11/2022 | | |
| CN | 112195152 B | 4/2023 | | |
| CN | 114736870 B | 11/2023 | | |
| JP | 2012165719 A | 9/2012 | | |
| WO | 2021179354 A1 | 9/2021 | | |
| WO | 2022160368 A1 | 8/2022 | | |

OTHER PUBLICATIONS

Chen et al (The Protein Journal (2021) 40:108-118, Doi: 10.1007/s10930-020-09949-2, Published online: Jan. 2, 2021) (Year: 2021).*
Janik et al (Biosci. Rep. (2016) / 36 / art:e00423 / doi 10.1042/BSR20160208) (Year: 2016).*
Li, Yingmei et al., In vitro Chemotherapeutics Susceptibility Studies on Primary Human Ovarian Cancer Cells and Its Clinical Application, Pharmacy Today, vol. 26, No. 5, May 31, 2016.
Ji, Xiaoxin et al., Establishment of a novel experimental liver metastasis model of human pancreatic cancer in vitro, Chin J Hepatobiliary Surg, No. 12, 2004-12-30.
Maria Angela Masini et al.,Prolonged exposure to simulated microgravity promotes stemness impairing morphological, metabolic and migratory profile of pancreatic cancer cells: a comprehensive proteomic, lipidomic and transcriptomic analysi, Cellular and Molecular Life Sciences, vol. 79, Apr. 7, 2022.
Liu, Jianfu et al. HuazhongUniversity ofScience andTechnology Press, Cell Engineering, the1st Edition, pp. 224-225, Jun. 30, 2014.
Xu, Fan, "The effect of microgravity on cell growth", Journal of Hubei University of Science and Technology (Medical Sciences) , vol. 33, Issue 2, Dec. 31, 2019.
Wilding, J.L. and Bodmer, W.F. Cancer cell lines for drug discovery and development, Cancer Res. 74, 2377--2384 (2014).
Wright, W.E. and Shay, J.W., The two-stage mechanism controlling cellular senescence and i mMortalization, Exp. Gerontol. 27, 383--389 (1992).

\* cited by examiner

*Primary Examiner* — Peter Paras, Jr.
*Assistant Examiner* — Khoa Nhat Tran
(74) *Attorney, Agent, or Firm* — IPRO, PLLC; Na Xu

(57)          ABSTRACT
A cultivation method for simulated microgravity-induced reprogramming of primary cancer cells and related culture media and reagents are in the field of biotechnology. A multi-directional G-force generator is used to simulate a $10^{-3}$ g microgravity environment, inducing reprogramming of cancer/cancer-adjacent tissue cells derived from patients, maintaining stemness of primary cell populations, and achieving rapid, long-term, high-fidelity cultivation of tissue cells from patients. Using this cultivation method, $10^6$ cells can be obtained within 7 days from a 1 mm$^3$ tissue block acquired during surgery for drug screening. Specially formulated culture media, washing solutions, and digestion solutions are also provided, effectively solving problems of contamination susceptibility and difficult digestion of clinical samples. The established cancer cell models maintain highly similar genetic characteristics to the original tissue and can reflect differences in drug sensitivity between different patients, providing a powerful tool for precision cancer treatment.

5 Claims, 17 Drawing Sheets

Samples from the same breast cancer patient

Samples from the same breast cancer patient

| Cell count (number) | Type of injected cells | | | | | |
|---|---|---|---|---|---|---|
| | CRC 2nd generation | SMGIR 2nd generation | CRC 4th generation | SMGIR 4th generation | CRC 6th generation | SMGIR 6th generation |
| 1000 | 3/5 | 3/5 | 5/5 | 5/5 | 3/5 | 5/5 |
| 500 | 2/5 | 2/5 | 4/5 | 3/5 | 1/5 | 4/5 |
| 250 | 0/5 | 1/5 | 3/5 | 3/5 | 0/5 | 2/5 |
| TCF (95% CI) | 1/543 (1/3141-1/1306) | 1/467 (1/2399-1/1058) | 1/135 (1/548-1/272) | 1/177 (1/697-1/351) | 1/649 (1/4510-1/1711) | 1/166 (1/656-1/329) |
| p value | | | | | | p=0.044 (vs.CRC 6th generation) |

A

Samples from the same breast cancer patient

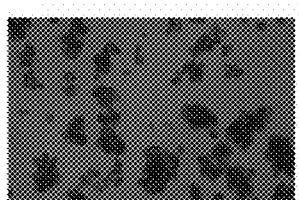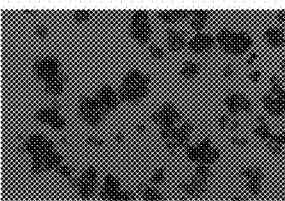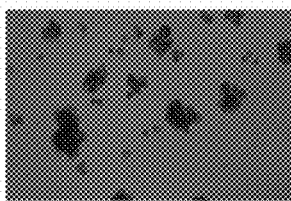

| Fresh tissue | Tissue after 6 months of cryopreservation | Re-cultivation of cells after cryopreservation |
|---|---|---|

| | Breast Cancer (2023) Guidelines of Chinese Society of Clinical Oncology (CSCO) | | |
|---|---|---|---|
| | CATEGORY | CHEMOTHERAPY DRUGS | CAS NO. |
| 1 | Topoisomerase-targeted drugs | Epirubicin hydrochloride | 56390-09-1 |
| 2 | | Pirarubicin hydrochloride | 95343-20-7 |
| 3 | | Doxorubicin hydrochloride | 25316-40-9 |
| 4 | Apoptosis-related targeted drugs | Docetaxel | 114977-28-5 |
| 5 | Autophagy-related targeted drugs | Paclitaxel | 33069-62-4 |
| 6 | DNA-binding drugs | Cyclophosphamide | 50-18-0 |
| 7 | | Carboplatin | 41575-94-4 |
| 8 | | 5-Fluorouracil | 51-21-8 |

Epirubicin hydrochloride

FIG. 12B

Cyclophosphamide

METHOD FOR CULTURING PRIMARY CANCER CELLS THROUGH SIMULATED MICROGRAVITY-INDUCED REPROGRAMMING AND APPLICATIONS THEREOF

CROSS-REFERENCE TO RELATED APPLICATIONS

The present invention claims the benefit and priority of Chinese patent applications CN202410683596.3 and CN202410683594.4, both filed on May 30, 2024, respectively entitled "method for culturing primary cancer cells through simulated microgravity-induced reprogramming and applications thereof" and "culture medium and related reagents for culturing cancer cells in microgravity environment and applications thereof". The entire contents of the above applications are incorporated herein by reference for all purposes.

TECHNICAL FIELD

The present invention relates to the field of biotechnology, specifically to a method for culturing primary cancer cells through simulated microgravity-induced reprogramming and applications thereof.

BACKGROUND

Cancer is a major disease affecting human health. Therefore, exploring effective cancer treatment strategies, improving cancer treatment efficacy, and extending patient survival time are crucial for comprehensively advancing healthcare development. Chemotherapy and targeted therapy remain the main systemic treatment approaches for breast cancer. However, due to individual patient differences and tumor heterogeneity, different breast cancer patients respond differently to chemotherapy drugs/targeted drugs, and the same patient may exhibit significant variations in response to these drugs at different treatment stages, ultimately leading to ineffective medication for some patients. Ineffective medication not only seriously affects the treatment outcome of breast cancer but also brings enormous physical damage and economic burden to patients. Therefore, personalized precision treatment has become the development direction for breast cancer treatment: by formulating individualized medication plans for each patient to minimize iatrogenic damage, minimize medical expenditure, and maximize patient benefits.

Therefore, using tumor models to test drug efficacy has become a common reference in clinical medication.

Tumor cell lines are the earliest and most mature tumor models, with characteristics of easy operation, low cost, and high reproducibility of experimental results, making them the pillar of tumor research over the past decades. However, long-term in vitro culture leads to significant differences from the original tumor tissue in terms of tumor heterogeneity and tumor microenvironment, and the lack of normal cancer-adjacent tissue controls limits their application in drug screening experiments.

Patient-derived primary tumor cells have the advantages of easy operation and low cost similar to tumor cell lines, while also retaining the heterogeneity characteristics of the patient's tumor to some extent. However, their low culture success rate and insufficient proliferation ability prevent long-term expansion, hindering the application of primary tumor cells in breast cancer in vitro research.

3D tumor organoids retain the original tumor heterogeneity while simulating the interaction between tumor cells and extracellular matrix. However, the culture time of organoids from different patients varies greatly, which affects clinical treatment decision-making to some extent. Additionally, organoids cannot simulate the interaction between stromal cells such as fibroblasts and tumor cells, and their culture cost is much higher than the previous two models.

Patient-derived xenograft (PDX) models address the shortcoming of 3D tumor organoids in that they cannot simulate the interaction between tumors and stromal cells, better preserving tumor heterogeneity. However, during the culture process, fibroblasts from the patient-derived tumor tissue are gradually replaced by mouse fibroblasts, leading to structural and functional differences between the PDX model and the original tumor tissue. In addition, the long construction period and relatively high cost are also its shortcomings.

In the CRC model, cesium γ-ray-irradiated Swiss-3T3-J2 mouse embryonic fibroblasts are co-cultured with human tumor cells or normal cells. By adding the ROCK inhibitor Y-27632, patient-derived primary cells acquire partial stem cell-like properties and the capacity for indefinite proliferation in vitro. This technology not only retains the advantages of easy operation and low cost of tumor cell line culture but also ensures high consistency and drug sensitivity characteristics between CRC and the original tumor tissue, while well simulating the interaction between tumor cells and fibroblasts. More importantly, compared with the PDX model, under suitable culture conditions, this technology can obtain a large number of tumor cells in a short period, meeting the needs of formulating individualized medication plans for each patient clinically. Additionally, normal cancer-adjacent tissue cells cultured using this technology can also be used to predict drug side effects, thereby providing prediction results for both drug efficacy and safety for clinical decision-making.

Although the CRC cell culture technology has broad application prospects in future cancer research and clinical treatment, there are still many technical problems and limitations. At the theoretical level, the molecular mechanism of tumor cell reprogramming is still unclear; at the technical level, the tumor cell reprogramming process is highly dependent on mouse embryonic fibroblasts and ROCK inhibitors, and these factors may have a significant impact on tumor cell proliferation, invasion, apoptosis, and drug sensitivity, thus affecting the accuracy of CRC cells as a tumor model in cancer research.

The tumor cell population contains a small proportion of cells with self-renewal ability and unlimited proliferation potential, namely cancer stem cells (CSC). The existence and maintenance of stemness of cancer stem cells are crucial for the successful culture of patient-derived primary tumor cells. The inventors found that specific tumor microenvironments (such as hypoxic environments) can alter the redox homeostasis and metabolic pattern of breast cancer cells, the activity of the second messenger calcium ion signaling pathway, phosphorylation networks and signal transduction preferences, chromatin epigenetic modifications, telomerase activity, and nuclear translocation of key transcription factors, causing an increase in the expression of cell pluripotency factors, inducing breast cancer cells to transform into breast cancer stem cells through a reprogramming process, thereby increasing the proportion of stem cells in the breast cancer cell population. This research provides a molecular basis for analyzing the tumor cell reprogramming process and offers a new approach for successfully culturing and long-term expansion of patient-derived primary breast cancer cells, that is, by changing the growth environment of cells, inducing some primary breast cancer cells to undergo reprogramming and transform into breast cancer stem cells, increasing the proportion of breast cancer stem cells, thereby achieving long-term in vitro expansion of patient-derived primary breast cancer cells.

Additionally, with the development of space science and technology, the impact of the microgravity environment on human physiological functions is becoming a research hotspot in the biomedical field. Space biology research indicates that gravity changes can lead to changes in various biological properties of tumor cells, including changes in tumor cell stemness. In previous research, the inventors found that adherent breast cancer cells, after being cultured in a microgravity environment for a period, could float in the culture medium and self-assemble into 3D spherical structures, and these 3D spheres had biological properties similar to cancer stem cells.

However, various tumor models in current existing technologies still have many problems, especially the lack of in vitro cell models that can accurately reflect the true situation of tumors in the human body, which has become a major obstacle in the development of precision cancer treatment. Therefore, clarifying the molecular mechanism of the tumor cell reprogramming process and developing a new generation of in vitro tumor models that can accurately reflect the true situation of tumors in vivo to meet the precision treatment needs of individual cancer patients is necessary and urgent.

SUMMARY

Given that current existing technologies lack in vitro cell models that can accurately reflect the true situation of tumors in the human body, and this deficiency has become a major obstacle in the development of precision cancer treatment, in response to the many problems existing in current tumor models, the inventors of the present application have developed a new type of primary cancer cell culture technology that uses a multi-directional G-force generator to simulate a $10^{-3}$ g microgravity environment, inducing reprogramming of patient-derived cancer/adjacent tissue cells, maintaining the stemness of primary cell populations, and achieving rapid, long-term, and high-fidelity culture of patient-derived cancer/adjacent tissue cells. The simulated microgravity-induced reprogramming (SMGIR) cultivation method of the present invention provides for the digestion and culture of surgical tissue specimens approximately 1 mm³ in volume, thereby generating $10^6$ cells within 7 days, this cell quantity being sufficient for performing in vitro drug screening assays.

According to a first aspect of the present application, a cultivation method for simulated microgravity-induced reprogramming of primary cancer cells is provided, wherein the cultivation method comprises a step of using a multi-directional G-force generator to simulate a space microgravity environment for cancer cell cultivation.

Optionally, the microgravity environment is $10^{-3}$ g with a fluctuation range of plus or minus 10%.

Optionally, the cultivation duration in the microgravity environment is 6.5~7.5 days.

Optionally, the cultivation method employs a Gravite® gravity control system, wherein the Gravite® gravity control system is configured with an outer shaft rotation speed of maximum 8 rpm and minimum 6 rpm for the rotating frame, and an inner shaft rotation speed of maximum 5 rpm and minimum 3 rpm.

Optionally, a culture medium used in the cultivation method comprises: 310~350 mL DMEM, 100~120 mL Ham's F12 nutrient mixture, 40~60 mL fetal bovine serum (FBS), 4~6 mL 200 mM glutamine solution, 4~6 mL penicillin-streptomycin mixture, 400~600 μL hydrocortisone/epidermal growth factor solution, 240~260 μL 10 mg/mL insulin, 4~6 μL 25 mg/ml amphotericin B, 90~110 μL 50 mg/mL gentamicin, 0.5~1.5 μL 5 mg/ml cholera toxin, and 480~520 μL 10 mM Y-27632.

Optionally, the cancer cells in the cultivation method are derived from cancerous tissue/cancer-adjacent tissue obtained from patients during surgery.

Optionally, cancer cells/cancer-adjacent cells to be cultivated are obtained after digestion and washing of the cancerous tissue/cancer-adjacent tissue;

washing solutions used for washing comprise solution A, solution B, solution C, and solution D, wherein the solution A comprises: 400~600 mL PBS buffer, 4~6 mL penicillin-streptomycin mixture, and 4~6 μL 25 mg/mL amphotericin B; the solution B comprises: 400~600 mL of the aforementioned culture medium and 8~12 mL penicillin-streptomycin mixture; the solution C is penicillin-streptomycin mixture; and the solution D is 0.04~0.06 wt % trypsin solution.

Optionally, the washing comprises the following steps:

S1: centrifuging a tumor tissue sample after digestion, discarding a resulting tissue digestion solution, thoroughly washing cells by pipette trituration using the solution A; centrifuging and discarding the solution A; resuspending the cells in the solution B and culturing;

S2: observing the next day, if the culture medium is turbid but no obvious fungal hyphae are present: aspirating and discarding the solution B from flask; thoroughly washing cells by pipette trituration using the solution A; aspirating and discarding the solution A; repeating the above operations 2~4 times, then continuing cultivation using the solution B; if the culture medium is turbid and obvious fungal hyphae are present: aspirating and discarding the solution B from flask; thoroughly washing the cells by pipette trituration using the solution A; aspirating and discarding the solution A; thoroughly washing the cells by pipette trituration using the solution C; aspirating and discarding the solution C; thoroughly washing the cells by pipette trituration using the solution D for 1~3 min; aspirating and discarding the solution D; thoroughly washing the cells by pipette trituration using the solution A; aspirating and discarding the solution A; repeating the above operations 2~4 times, then continuing cultivation using the solution B;

S3: observing daily and repeating the above S2 operation, until the cells recover to a normal sterile state after three days, then using culture medium for routine cultivation.

Optionally, the digestion solution used for digestion comprises: 800~1000 μL Collagenase/Hyaluronidase DMEM solution, 7800~8400 μL of the aforementioned culture medium, and 2~5 mL of HBSS solution of dispase, wherein a concentration of the dispase in HBSS is 4~6 U/mL.

According to a second aspect of the present application, a culture medium for culturing cancer cells in a microgravity environment is provided, wherein the culture medium comprises: 310~350 mL DMEM, 100~120 mL Ham's F12 nutrient mixture, 40~60 mL fetal bovine serum (FBS), 4~6 mL 200 mM glutamine solution, 4~6 mL penicillin-strep-tomycin mixture, 400~600 μL hydrocortisone/epidermal growth factor solution, 240~260 μL 10 mg/mL insulin, 4~6 μL 25 mg/mL amphotericin B, 90~110 μL 50 mg/mL gentamicin, 0.5~1.5 μL 5 mg/mL cholera toxin, and 480~520 μL 10 mM Y-27632.

It should be noted that the amounts of components in the culture medium of the present application are not unique. For example, a person skilled in the art can adjust the amounts of various components in the culture medium proportionally according to the usage situation. The above expression is only one way of indicating the components used in the culture medium and the proportions of each component. It should be understood by a person skilled in the art that other culture medium compositions essentially the same as the above culture medium, apart from the above situation, should fall within the scope of protection of the present application.

According to a third aspect of the present application, a use of the above culture medium in culturing cancer cells or tissues in a microgravity environment is provided.

Optionally, the cancer cells or tissues originate from breast cancer, ovarian cancer, or lung cancer.

Optionally, the culture medium comprises: 310~350 mL DMEM, 100~120 mL Ham's F12 nutrient mixture, 40~60 mL fetal bovine serum (FBS), 4~6 mL 200 mM glutamine solution, 4~6 mL penicillin-streptomycin mixture, 400~600 μL hydrocortisone/epidermal growth factor solution, 240~260 μL 10 mg/mL insulin, 4~6 μL 25 mg/mL amphotericin B, 90~110 μL 50 mg/mL gentamicin, 0.5~1.5 μL 5 mg/mL cholera toxin, and 480~520 μL 10 mM Y-27632.

Optionally, the culture medium can induce breast cancer cell reprogramming when culturing breast cancer cells in a microgravity environment; the microgravity environment is simulated as a $10^{-3}$ g microgravity environment using a multi-directional G-force generator.

According to a fourth aspect of the present application, a cancer cell washing solution is provided, wherein the cancer cell washing solution comprises solution A, solution B, solution C, and solution D;

wherein the solution A comprises: 400~600 mL PBS buffer, 4~6 mL penicillin-streptomycin mixture, and 4~6 μL 25 mg/mL amphotericin B;

wherein the solution B comprises: 400~600 mL of the aforementioned culture medium and 8~12 mL penicillin-streptomycin mixture;

wherein the solution C is penicillin-streptomycin mixture;

wherein the solution D is 0.04~0.06 wt % trypsin solution.

It should be noted that the amounts of components in the washing solution of the present application are not unique. For example, a person skilled in the art can adjust the amounts of various components in the washing solution proportionally according to the usage situation. The above expression is only one way of indicating the components used in the washing solution and the proportions of each component. It should be understood by a person skilled in the art that other washing solution compositions essentially the same as the above washing solution, apart from the above situation, should fall within the scope of protection of the present application.

According to a fifth aspect of the present application, a use of the above washing solution in decontamination of cancer cells or tissues is provided.

Optionally, the cancer cells or tissues originate from breast cancer, ovarian cancer, or lung cancer.

According to a sixth aspect of the present application, a method of using the above washing solution is provided, wherein the method of use comprises the following steps:

S1: centrifuging a tumor tissue sample after digestion, discarding a resulting tissue digestion solution, thoroughly washing resulting cells using the solution A; centrifuging and discarding the solution A; resuspending the cells in solution B and culturing;

S2: observing the next day, if the culture medium is turbid but no obvious fungal hyphae are present: aspirating and discarding the solution B from flask; thoroughly washing cells by pipette trituration using the solution A; aspirating and discarding the solution A; repeating the above operations 2~4 times, then continuing cultivation using the solution B; if the culture medium is turbid and obvious fungal hyphae are present: aspirating and discarding the solution B from flask; thoroughly washing the cells by pipette trituration using the solution A; aspirating and discarding the solution A; thoroughly washing the cells by pipette trituration using the solution C; aspirating and discarding the solution C; thoroughly washing the cells by pipette trituration using the solution D for 1~3 min; aspirating and discarding the solution D; thoroughly washing the cells by pipette trituration using the solution A; aspirating and discarding the solution A; repeating the above operations 2~4 times, then continuing cultivation using the solution B;

S3: observing daily and repeating the above S2 operation until the cells recover to a normal sterile state after three days, that is, the culture medium is clear, and no bacteria or fungal hyphae are observed in the field of view under the microscope, then using culture medium for routine cultivation.

The present application is based on microgravity cultivation of cancerous tissue/cancer-adjacent tissue obtained from patients during surgery to obtain cancer cell models. The cancerous tissue/cancer-adjacent tissue obtained during surgery varies in condition. For example, for cancerous tissue obtained from ovarian cancer, surgery requires an open abdominal operation, and due to the growth position of ovarian cancer, the removed tissue is very susceptible to contamination. Therefore, thorough decontamination operations must be performed, otherwise it is extremely easy to cause microgravity cultivation failure and consequently cancer cell model establishment failure, which is very wasteful for the precious cancerous tissue/cancer-adjacent tissue from patients' surgery. For breast cancer tissue, although its growth environment is more stable and less susceptible to contamination, there is still a risk of contamination during surgery and tissue preservation or transfer. Therefore, if the problem of contamination leading to cultivation failure is not solved, it is impossible to truly apply cancerous tissue/cancer-adjacent tissue obtained from patients' surgery to establish primary cancer cell models in a microgravity environment.

According to a seventh aspect of the present application, a cancer cell digestion solution is provided, wherein the digestion solution comprises: 800~1000 μL Collagenase/Hyaluronidase DMEM solution, 7800~8400 μL of the aforementioned culture medium, and 2~5 mL of HBSS solution of dispase, wherein a concentration of the dispase in HBSS is 4~6 U/mL.

It should be noted that the amounts of components in the digestion solution of the present application are not unique. For example, a person skilled in the art can adjust the amounts of various components in the digestion solution proportionally according to the usage situation. The above expression is only one way of indicating the components used in the digestion solution and the proportions of each component. It should be understood by a person skilled in the art that other digestion solution compositions essentially the same as the above digestion solution, apart from the above situation, should fall within the scope of protection of the present application.

According to an eighth aspect of the present application, a use of the above cancer cell digestion solution in digesting cancer cells or tissues is provided.

Optionally, the cancer cells or tissues originate from breast cancer, ovarian cancer, or lung cancer.

According to a ninth aspect of the present application, a method of using the above digestion solution is provided, wherein the method comprises the following steps:

1) sterilizing ophthalmic forceps and blades using anhydrous ethanol;

2) transferring the prepared digestion solution into a centrifuge tube;

3) using the ophthalmic forceps to clamp tissue, placing the tissue in a sterile culture dish, subsequently mincing the tissue into millet-sized pieces using the blade;

4) transferring the minced tissue mash into the centrifuge tube containing the digestion solution, tightening the tube cap, wrapping with sealing film, placing on a 36~38° C. shaker at 200~250 rpm for 3.5~4.5 h to thoroughly digest the tissue.

According to a tenth aspect of the present application, a kit is provided, wherein the kit contains the above culture medium, and/or the above washing solution, and/or the above cancer cell digestion solution.

According to an eleventh aspect of the present application, a use of any of the above cultivation methods for simulated microgravity-induced reprogramming of primary cancer cells in establishing cancer patient tumor models, screening cancer treatment drugs, or developing anti-cancer drugs is provided.

According to a twelfth aspect of the present application, a cancer cell product prepared by any of the above cultivation methods for simulated microgravity-induced reprogramming of primary cancer cells is provided.

According to a thirteenth aspect of the present application, a use of the above cancer cell product in establishing cancer patient tumor models, screening cancer treatment drugs, or developing anti-cancer drugs is provided.

The beneficial effects of the present application are as follows:

the present application establishes a new, efficient, low-cost, and individualized tumor model that highly conforms to the patient's pathophysiological state, which can effectively promote the precision treatment process of cancer, especially breast cancer, ovarian cancer, and lung cancer. In addition, primary cells cultured using SMGIR technology still possess good proliferation ability after multiple passages and liquid nitrogen cryopreservation and resuscitation, and maintain high consistency with the patient's original tissue genotype. These characteristics lay the foundation for later establishment of regional or international "living" banks of cancer patient biological samples. The present application, relying on rich clinical resources, will achieve the upgrading of tumor cell models, this source resource, through technological innovation, and can greatly promote the transformation and upgrading of cancer research and anti-cancer drug development worldwide.

This research promotes the process of individualized tumor treatment by developing a "simulated microgravity-induced reprogramming of primary breast cancer cells" cultivation method. This research aims to achieve the upgrading of tumor cell models through technological innovation, promoting cancer research and drug development for the genetic characteristics of tumor patients in different regions from the source.

BRIEF DESCRIPTION OF THE DRAWINGS

The drawings described herein are provided to offer further understanding of the present application, constituting a part of the present application. The illustrative embodiments of the present application and their descriptions are used to explain the present application and do not constitute improper limitations on the present application. In the drawings:

FIG. 11 shows the detection results of repeated cultivation capability of tumor cell models as related to the present application.

FIG. 12A shows a list of chemotherapy drugs recommended in the 2023 breast cancer treatment guidelines from the Chinese Society of Clinical Oncology (CSCO).

FIG. 12B shows the molecular structure diagram of epirubicin hydrochloride.

FIG. 12C shows the molecular structure diagram of cyclophosphamide.

FIGS. 12D to 12O show the results of drug trials (sensitivity tests) of breast cancer cells and normal breast tissue cells cultured by SMGIR against two chemotherapy drugs (epirubicin and cyclophosphamide). Wherein, FIGS. 12D to 12I show the dose-response relationships of breast cancer cells (D, F, H) and normal breast tissue cells (E, G, I) from three patients (38, 7, and 71) to epirubicin; FIGS. 12J to 12O show the dose-response relationships of breast cancer cells (J, L, N) and normal breast tissue cells (K, M, O) from the same three patients (38, 7, and 71) to cyclophosphamide.

DESCRIPTION OF THE PREFERRED EMBODIMENTS

The present application will be described in detail in conjunction with embodiments below, but the present application is not limited to these embodiments. Unless otherwise specified, the materials and catalysts in the embodiments of the present application are all purchased through commercial channels.

Tumor cell models are indispensable core elements in cancer research and drug development. However, the currently widely used tumor cell line models cannot reflect characteristics such as tumor heterogeneity and tumor microenvironment, and can no longer meet the needs of the era of precision cancer treatment. Therefore, developing new individualized tumor models is of great significance for promoting precision cancer treatment. With the development of space science and technology, the effects of microgravity environment on human physiological functions are becoming research hotspots in the biomedical field. Space biology research indicates that gravity changes can lead to changes in various biological properties of tumor cells, including changes in tumor cell stemness. Through research, the inventors discovered that adherent breast cancer cells, after being cultured in a microgravity environment for a period of time, can suspend in the culture medium and self-assemble into 3D spheroid structures, and these 3D spheroids have biological properties similar to those of tumor stem cells.

Based on this discovery, the inventors further explored the phenotypic basis for simulated microgravity environment inducing reprogramming of primary breast cancer cells into breast cancer stem cells. Based on these studies, the inventors believe that simulated microgravity environment can induce reprogramming of primary breast cancer cells, promote the transformation of breast cancer cells into breast cancer stem cells, and by using simulated microgravity-induced reprogramming cultivation method, through increasing the proportion of stem cells in the breast cancer cell population, maintain the viability of cancer cell populations, thereby achieving long-term in vitro expansion of primary breast cancer cells derived from patients.

Figure 1:
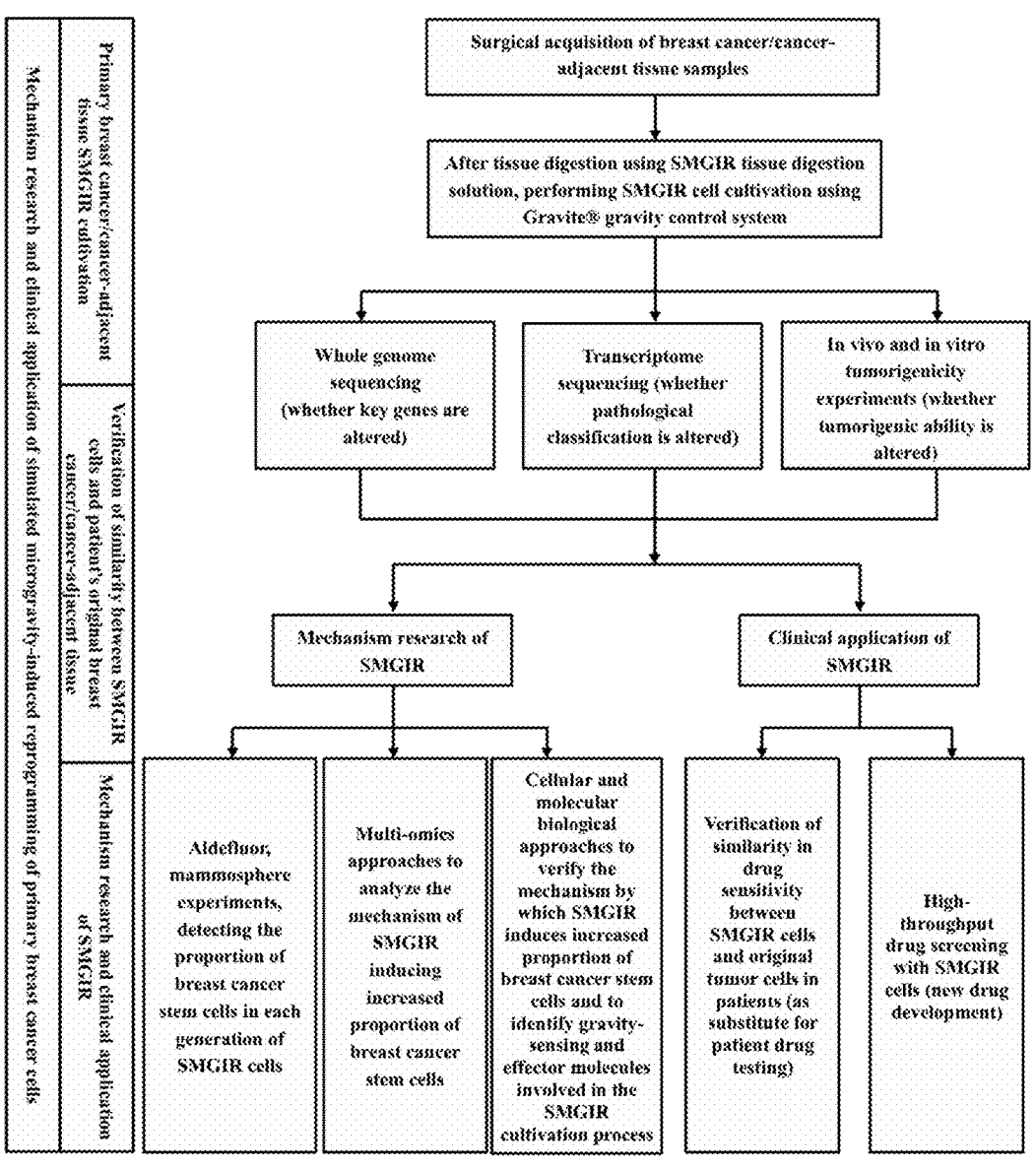
FIG. 1 is a schematic diagram of the research pathway of the present application.

In the present application, starting from the 3D spheroids with properties similar to tumor stem cells that can be obtained through cultivation in simulated microgravity environment, the inventors successfully established a new primary cancer/cancer-adjacent tissue cell cultivation method based on simulated microgravity-induced reprogramming, and analyzed the molecular mechanism of simulated microgravity inducing reprogramming of primary cancer cells, explored the clinical application of microgravity-induced reprogramming, breaking through the predicament that existing tumor models cannot meet the needs of precision cancer treatment, promoting the process of precision cancer treatment at the source. The research pathway of the inventors is shown in FIG. 1. In addition, the inventors also extended this cultivation method to primary ovarian cancer/cancer-adjacent tissue cells and lung cancer/cancer-adjacent tissue cells, successfully obtaining corresponding cancer cell models, and obtaining a considerable number of tumor cells.

Different from the currently existing mature in vitro cell models, the cell models in the present application are obtained through microgravity environment cultivation based on patient cancer/cancer-adjacent tissue samples from surgery. On one hand, the growth state and conditions of tissue cells from patients themselves may differ greatly. For example, ovarian cancer tissue requires open abdominal operations during surgery, and cancer tissue growth may develop to close to bacterial environments (such as the vagina), so the tissue or cells obtained after surgery are very susceptible to bacterial contamination. On the other hand, cancer/cancer-adjacent tissue samples from patients are very rare and small in quantity, and cannot be repeatedly obtained, so these samples are very precious. Therefore, the processing and cultivation conditions are very strict, requiring high stability of successful cultivation. Lastly, the present application focuses on cultivation of cancer tissue/cancer-adjacent tissue in a microgravity environment, which differs from conventional cultivation conditions, so there are different requirements for culture medium and cultivation conditions.

The chemical reagent specifications involved in the present application are shown in Table 1, Table 2, and Table 3.

TABLE 1

| Sources of Culture Medium Reagents | | |
| --- | --- | --- |
| Name | Brand | Catalog Number |
| DMEM | Vivacell | C3113 |
| Ham's F-12 nutrient mixture | Gibco | 11765054 |
| Fetal bovine serum (FBS) | Gibco | 10091148 |
| L-glutamine (200 mM) | Solarbio | G0200 |
| Penicillin-streptomycin mixture (100×) | Solarbio | P1400 |
| Hydrocortisone/EGF solution | Hydrocortisone purchased from MCE; EGF purchased from Stemcell | Hydrocortisone catalog number: HY-N0583, EGF catalog number: 78006.1 |

TABLE 1-continued

| Sources of Culture Medium Reagents | | |
| --- | --- | --- |
| Name | Brand | Catalog Number |
| Insulin | Procell | PB180432 |
| Amphotericin B | MCE | HY-K1052 |
| Gentamicin sulfate solution | Solarbio | L1312 |
| Cholera toxin | MCE | HY-P1446 |
| Y-27632 | ENZO | ALX-270-333-M025 |

Wherein, preparation steps of the hydrocortisone/EGF solution are as follows: mixing 100 mg of hydrocortisone powder with 10 mL of anhydrous ethanol to prepare 10 mg/mL hydrocortisone solution; taking 1 mL of the above 10 mg/mL hydrocortisone solution, adding 19 mL of anhydrous ethanol to obtain 20 mL of 0.5 mg/mL hydrocortisone solution; combining 100 μg EGF with 1 mL of water to obtain 0.1 mg/mL EGF solution; taking 25 μL of the above EGF solution, adding 19 mL of DMEM to obtain EGF solution. Finally, combining 1 mL of 0.5 mg/mL hydrocortisone with 19 mL of EGF solution to prepare 20 mL of hydrocortisone/EGF solution, aliquoting and storing at −20° C. for later use.

TABLE 2

| Sources of Washing Solution Reagents | | |
| --- | --- | --- |
| Name | Brand | Catalog Number |
| 1 × PBS buffer (pH7.2~7.4) | Solarbio | P1020 |
| Penicillin-streptomycin mixture (100×) | Solarbio | P1400 |
| Amphotericin B | MCE | HY-K1052 |
| 0.05% Trypsin | Beyotime | C0202 |

TABLE 3

| Sources of Digestion Solution Reagents | | |
| --- | --- | --- |
| Name | Brand | Catalog Number |
| 10X Collagenase/hyaluronidase in DMEM | Stemcell | 07912 |
| 5 U/mL dispase in Hanks' Balanced Salt Solution | Stemcell | 07913 |

Wherein, penicillin-streptomycin mixture is a commonly used reagent in this field. In the present application, penicillin-streptomycin mixture contains penicillin at a concentration of 10 kU/mL and streptomycin at a concentration of 10 mg/mL; PBS buffer is a commonly used reagent in this field. In the present application, main components and concentrations in PBS buffer are $KH_2PO_4$ 1.8 mM, $Na_2HPO_4 \cdot 12H_2O$ 8.0 mM, NaCl 137.0 mM.

Example 1: Optimization of Microgravity Cultivation Conditions

The present application induced reprogramming of primary cancer cells derived from patients through a simulated microgravity environment to achieve long-term in vitro cultivation. To obtain optimal cultivation effects, the inventors first systematically optimized key parameters of microgravity cultivation. The following optimization experiments were mainly conducted using primary breast cancer cells obtained from surgical patients to ensure that the optimization results had direct reference value for clinical samples.

1) Selection and Parameter Setting of Microgravity Simulation System

The present application employed the Gravite® gravity control system for microgravity environment simulation. This system generated simulated microgravity effects in Earth's gravity environment through a rotation mechanism. After multiple experimental comparisons, the optimal rotation parameters were determined to be: outer shaft rotation speed of the rotating frame set to maximum 8 rpm and minimum 6 rpm, inner shaft rotation speed set to maximum 5 rpm and minimum 3 rpm, controlling the microgravity environment at $10^{-3}$ g, with fluctuations controlled within ±10% range.

The basic steps of microgravity cultivation were as follows: primary breast cancer cells that had undergone digestion treatment were inoculated into T25 culture flasks, allowed to completely adhere to the wall after static culture for 24 hours in a conventional $CO_2$ cell incubator, then the culture flasks were fixed on the rotating frame of the Gravite® gravity control system and placed in a $CO_2$ cell incubator for microgravity cultivation. Throughout the entire cultivation process, the incubator temperature was maintained at 37° C., $CO_2$ concentration at 5%, and relative humidity at 95%.

2) Optimization of Cultivation Duration

When cultivating primary breast cancer cells in a microgravity environment, the inventors found that cultivation duration had the most significant impact on the final results.

Figure 2:
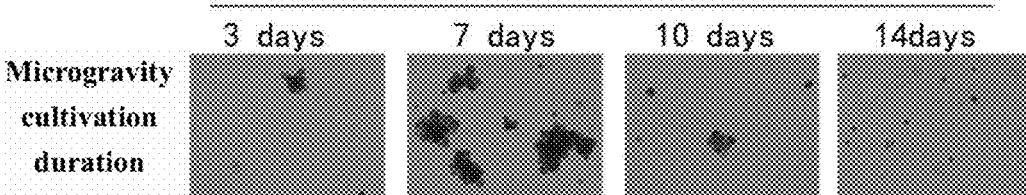
FIG. 2 is a result diagram showing cell model cultivation under different microgravity cultivation durations related to the present application.

As shown in FIG. 2, the inventors conducted comparative analyses of microgravity cultivation for 3 days, 7 days, 10 days, and 14 days on primary breast cancer cells from the same batch (from the same breast cancer patient). The results showed that at 7 days of cultivation, the cell count was highest, with both the total cell count and the cell count in individual spheroids reaching an optimal state. Therefore, cultivation for 6.5~7.5 days under microgravity conditions was ultimately determined as the standard cultivation duration, while other cultivation durations could not achieve cultivation results of the same quality.

To verify the universal applicability of this optimization result, the inventors also conducted similar experiments using primary ovarian cancer cells and lung cancer cells. The results similarly indicated that a cultivation duration of around 7 days was optimal, confirming that this parameter was applicable to various types of primary cancer cells.

The inventors speculated that the reason for this result was: 3 days of cultivation was not sufficient to complete the reprogramming process, and cells could not fully acquire stem cell characteristics; while cultivation durations exceeding 7 days would lead to excessive growth of cell spheres, insufficient internal nutrition and oxygen supply, ultimately resulting in poor cell condition or even apoptosis. The cultivation time of around 7 days was just right to allow primary cancer cells to complete the reprogramming process while maintaining good growth conditions.

Through the optimization of microgravity cultivation conditions described above, standardized experimental parameters were provided for subsequent cancer cell cultivation, ensuring the stability and reproducibility of cultivation results. Based on this, the culture medium formulation screening, optimization of washing solutions and digestion solutions, and cultivation experiments of different types of cancer cells in subsequent examples all utilized the optimized microgravity cultivation conditions mentioned above.

Example 2: Culture Medium Formulations and Experiments

Based on the microgravity cultivation conditions determined in Example 1 (outer shaft rotation speed of the Gravite® gravity control system at maximum 8 rpm and minimum 6 rpm, inner shaft rotation speed at maximum 5 rpm and minimum 3 rpm, microgravity environment at $10^{-3}$ g with fluctuation range of ±10%, cultivation duration of 6.5~7.5 days), the inventors further investigated culture medium formulations suitable for culturing tumor cells in a microgravity environment. Through extensive experimentation and repeated optimization, the inventors obtained the following culture medium formulations and their comparative effects.

Culture Medium 1 #

A culture medium for culturing cancer cells in a microgravity environment, comprising: 330 mL DMEM, 110 mL Ham's F12 nutrient mixture, 50 mL fetal bovine serum (FBS), 5 mL 200 mM glutamine solution, 5 mL penicillin-streptomycin mixture, 500 μL hydrocortisone/epidermal growth factor solution, 250 μL 10 mg/mL insulin, 5 μL 25 mg/mL amphotericin B, 100 μL 50 mg/mL gentamicin, 1 μL 5 mg/mL cholera toxin, and 500 μL 10 mM Y-27632.

Culture Medium 2 #

A culture medium for culturing cancer cells in a microgravity environment, comprising: 310 mL DMEM, 100 mL Ham's F12 nutrient mixture, 60 mL fetal bovine serum (FBS), 4 mL 200 mM glutamine solution, 6 mL penicillin-streptomycin mixture, 400 μL hydrocortisone/epidermal growth factor solution, 260 μL 10 mg/mL insulin, 4 μL 25 mg/mL amphotericin B, 110 μL 50 mg/mL gentamicin, 1.5 μL 5 mg/mL cholera toxin, and 480 μL 10 mM Y-27632.

Culture Medium 3 #

A culture medium for culturing cancer cells in a microgravity environment, comprising: 350 mL DMEM, 120 mL Ham's F12 nutrient mixture, 40 mL fetal bovine serum (FBS), 6 mL 200 mM glutamine solution, 4 mL penicillin-streptomycin mixture, 600 μL hydrocortisone/epidermal growth factor solution, 240 μL 10 mg/mL insulin, 6 μL 25 mg/mL amphotericin B, 90 μL 50 mg/mL gentamicin, 0.5 μL 5 mg/mL cholera toxin, and 520 μL 10 mM Y-27632.

Comparative Culture Medium D1 #

BLM culture medium from patent CN109355261B, comprising: DMEM and serum-free medium SFM mixed at a volume ratio of 1:3, with the addition of 5% (v/v) fetal bovine serum, as well as 5 μg/mL insulin, 25 ng/ml hydrocortisone, 0.1 nM cholera toxin, 0.125 ng/mL epidermal growth factor, 10 mg/mL gentamicin, 250 ng/ml amphotericin B, 1 μM A83-01 selective inhibitor, 5 μM Y-27632, 3 μM isoproterenol, filtered through a 0.22 μm pore size filter membrane.

Comparative Culture Medium D2 #

Culture medium from patent CN114736870B, comprising: Advanced DMEM/F12, and the following components based on Advanced DMEM/F12: 1 v % penicillin-streptomycin, 1 v % GlutaMAX, 1 v % HEPES buffer, 100 ng/mL fibroblast growth factor, 50 ng/mL EGF, 0.1 μmol/L A83-01, 500 ng/mL Wnt3a recombinant protein, 0.1 μg/mL Noggin recombinant protein, 0.1 μg/mL R-spondin-1 recombinant protein, 1 mMol/L N-acetylcysteine, 10 mmol/L Nicotinamide, 2 v % B27 supplement, 1 μmol/L dexamethasone, 1 v % N-2 supplement, 10 μmol/L Y-27632.

Comparative Culture Medium D3 #

FM culture medium from patent WO 2021/179354, comprising: 65 v % DMEM culture medium, 10 v % fetal bovine serum, 25 v % Ham's F12 nutrient solution, 25 ng/mL hydrocortisone, 0.125 ng/mL epidermal growth factor, 5 μg/mL insulin, 250 ng/ml amphotericin B, 10 μg/mL gentamicin, 0.1 nM cholera toxin, 10 M Y27632.

Comparative Culture Medium D4 #

HCCM culture medium from patent WO2021/179354, comprising: 1% (v/v) N-2, 10 ng/mL epidermal growth factor, 20 ng/mL hepatocyte growth factor, 20 ng/mL basic fibroblast growth factor, 250 ng/mL R-spondin1, 250 ng/mL glutamine, 1 μM non-essential amino acids, 5 ng/ml insulin, 10 μM Y-27632, 5 ng/ml IL-6, 90 v % DMEM/F12 culture medium, 10 v % fetal bovine serum, 400 ng/ml hydrocortisone, 1 v % streptomycin-penicillin, 0.1 v % Primocin, 2% (v/v) B27.

Comparative Culture Medium D5 #

Human colorectal cancer organoid culture medium from patent CN112195152B, comprising: B27, N-2, GlutaMAX, 5~15 nM Gastrin, 0.5~1.5 mM N-acetyl cysteine, 90~110 μg/mL gentamicin, 1~1.5 μg/mL amphotericin B, 90~110 μg/mL primocin, 8~15 μM SB202190, 5~15 UM Y-27632, 45~55 ng/mL EGF, 4~6 ng/mL FGF, 4~6% (v/v) FBS DMEM/F12 culture medium.

Culture Medium Screening and Comparison Experiments

Figure 3:
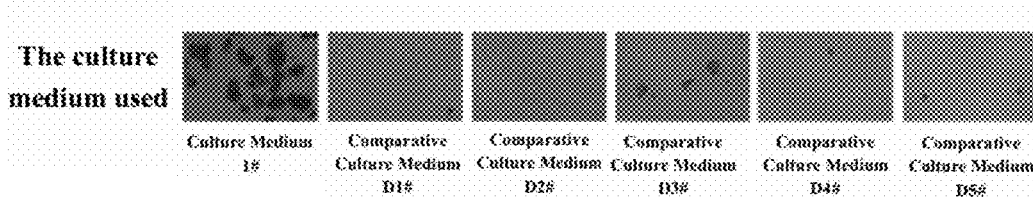
FIG. 3 shows cell cultivation results using different culture media for samples from the same breast cancer patient as related to the present application.

Culture Medium 1 # and Comparative Culture Media D1 #~D5 # were used to conduct cultivation comparisons under microgravity conditions on samples from the same breast cancer patient. The specific steps were as follows: breast cancer cells that had undergone digestion treatment were inoculated into T25 culture flasks containing different culture media, allowed to completely adhere to the wall after static culture for 24 hours in a conventional $CO_2$ incubator, then each culture flask was fixed on the rotating frame of the Gravite® gravity control system and cultured for 7 days under the microgravity conditions determined in Example 1, followed by observation and comparison of cell growth conditions. As shown in FIG. 3, according to the illustrated results, comparative culture media D1 #~D5 # all failed to achieve tumor cell cultivation in a microgravity environment. The results showed that only culture media 1 #, 2 #, and 3 # provided by the present application could successfully culture primary cells in a microgravity environment, while other culture media could not culture primary cells in a microgravity environment, with cells exhibiting non-proliferation or death.

The reasons for the different performances of various culture media in a microgravity environment were analyzed as follows:

in D1 #, 1 μM A83-01 selective inhibitor was added. A83-01 is an effective inhibitor of TGF-β type I receptor kinase ALK5, as well as ALK4 and ALK7, which can effectively reduce cell adhesion increased by TGF-β1. According to the results shown in FIG. 3, when using this culture medium, cells could not form spheres in a microgravity environment. It was speculated that this might be due to the addition of A83-01, which reduced intercellular adhesion, resulting in cells being unable to form spheres.

In D2 # and D4 #, 100 ng/ml and 20 ng/ml of fibroblast growth factor were added, respectively. Fibroblast growth factor, as a polypeptide secreted by the pituitary and hypothalamus, can promote fibroblast mitosis, while the proliferation of fibroblasts inhibits the growth of cancer cells. The inventors speculated that the fibroblast factors added therein led to the failure to achieve tumor cell cultivation in a microgravity environment.

D3 # had components relatively similar to culture medium 1 #, but the proportions of DMEM culture medium and F12 nutrient solution were different. In addition, D3 # did not contain penicillin-streptomycin mixture and glutamine solution, which might be the reason for the significantly fewer cells cultured in a microgravity environment in the D3 # results compared to culture medium 1 #.

In D5 #, the culture medium was human colorectal cancer organoid culture medium, so using it to culture non-colorectal cancer cells resulted in cells being unable to proliferate in vitro or death.

Through the above culture medium screening experiments, it was confirmed that the culture medium formulations provided by the present application (culture media 1 #, 2 #, 3 #) were particularly suitable for cultivating primary cancer cells in a microgravity environment, could effectively support the growth and reprogramming of cancer cells under microgravity conditions, and provided a critical cultivation foundation for the subsequent establishment of cancer cell models.

Example 3: Washing Solution Formulations and Decontamination Experiments

During the process of cultivating primary cancer cells in a microgravity environment, contamination of tissue samples presented a significant challenge. Fungal contamination was particularly problematic because culture media contaminated with fungi typically remained clear and transparent, and did not exhibit the major outbreak pattern seen with bacterial infections, making it difficult to detect in the early stages. When observed under a microscope, fungal contamination sometimes appeared filamentous, sometimes coral-like, and as cultivation time extended, very fine black filaments gradually developed.

In conventional cultivation processes, once fungal contamination was observed under the microscope, the culture was typically discarded directly, and the cultivation environment thoroughly disinfected and sterilized. However, the tumor cells cultivated in the present application came from precious tumor samples from patients after surgery. These samples were typically difficult to obtain and could not be repeatedly acquired, making them extremely valuable. At the same time, tumor samples collected during surgery were prone to fungal contamination due to factors such as the surgical process and the environment where tumor cells grew. Therefore, developing an effective washing solution and washing method was crucial for ensuring the success rate of microgravity cultivation.

Washing Solution 1 #

A cancer cell washing solution, comprising: solution A, solution B, solution C, and solution D; wherein the solution A comprised: 500 mL PBS buffer, 5 mL penicillin-streptomycin mixture, and 5 µL 25 mg/ml amphotericin B; the solution B comprised: 500 mL of culture medium 1 # from Example 1 and 10 mL penicillin-streptomycin mixture; the solution C was penicillin-streptomycin mixture; the solution D was 0.05 wt % trypsin solution.

Washing Solution 2 #

A cancer cell washing solution, comprising: solution A, solution B, solution C, and solution D; wherein the solution A comprised: 600 mL PBS buffer, 4 mL penicillin-streptomycin mixture, and 4 µL 25 mg/ml amphotericin B; the solution B comprised: 400 mL of culture medium 1 # from Example 1 and 8 mL penicillin-streptomycin mixture; the solution C was penicillin-streptomycin mixture; the solution D was 0.04 wt % trypsin solution.

Washing Solution 3 #

A cancer cell washing solution, comprising: solution A, solution B, solution C, and solution D; wherein the solution A comprised: 400 mL PBS buffer, 6 mL penicillin-streptomycin mixture, and 6 µL 25 mg/ml amphotericin B; the solution B comprised: 600 mL of culture medium 1 # from Example 1 and 12 mL penicillin-streptomycin mixture; the solution C was penicillin-streptomycin mixture; the solution D was 0.06 wt % trypsin solution.

Washing Method

A cancer tissue washing method, using washing solution from washing solution 1 #, comprising the following steps:

S1: after tissue digestion and centrifugation, discarding the tissue digestion solution, thoroughly washing cells by pipette trituration using 1 mL of the solution A; centrifuging and discarding the solution A; resuspending cells in an appropriate amount of the solution B and transferring to a T25 cell culture flask for cultivation.

S2: Observation and Assessment

Observing the next day, if the culture medium was turbid but no obvious fungal hyphae were present: aspirating and discarding the solution B from the flask; thoroughly washing cells by pipette trituration using the solution A; aspirating and discarding the solution A; repeating the above operations 2~4 times, then continuing cultivation using the solution B.

If the culture medium was turbid and obvious fungal hyphae were present: aspirating and discarding the solution B from the flask; thoroughly washing cells by pipette trituration using the solution A; aspirating and discarding the solution A; thoroughly washing cells by pipette trituration using the solution C; aspirating and discarding the solution C; thoroughly washing cells by pipette trituration using the solution D for 1~3 min; aspirating and discarding the solution D; thoroughly washing cells by pipette trituration using the solution A; aspirating and discarding the solution A; repeating the above operations 2~4 times, then continuing cultivation using the solution B.

S3: Observing daily and repeating the above operations until the cells recovered to a normal sterile state after three days, i.e., the culture medium was clear, and no bacteria or fungal hyphae were observed in the field of view under the microscope, then adding culture medium 1 # for routine cultivation.

Washing Effect Test

The inventors studied the decontamination effect of washing solution 1 # on fungi under microgravity cultivation conditions, observing the decontamination effect through the above washing method.

Figure 4A:
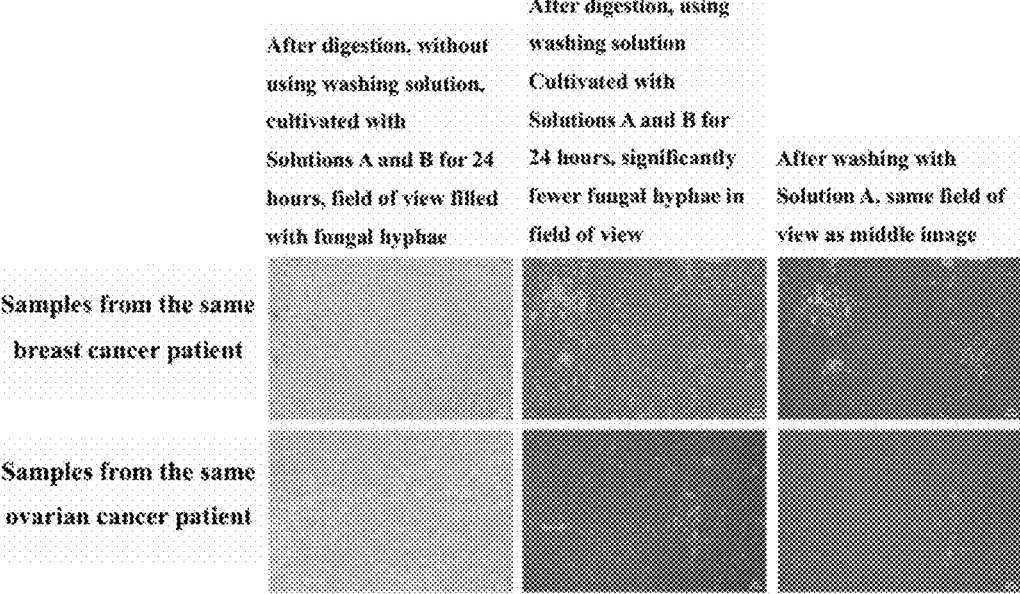
FIG. 4A shows the decontamination results of tumor cells as related to the present application, indicating that the washing solution of the present application can effectively remove fungi from primary breast cancer and ovarian cancer cells.
Figure 4B:
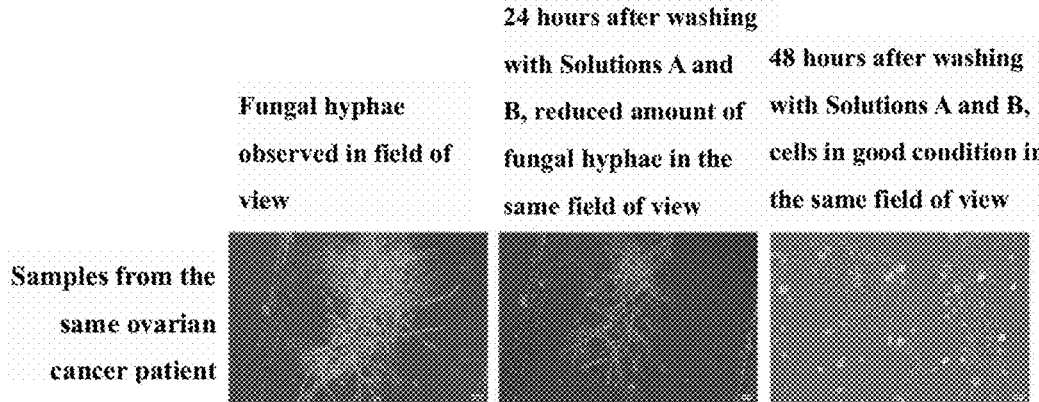
FIG. 4B shows the cultivation results of tumor cells as related to the present application, indicating that after removing fungi using the washing solution of the present application, cells can continue to grow normally.

The results are shown in FIG. 4A and FIG. 4B. According to the results shown in FIG. 4A, this washing solution effectively removed fungi from primary breast cancer and ovarian cancer cells. As shown in FIG. 4B, cells could continue to grow normally after fungal removal, thereby preserving precious tissue/cell samples from patients and avoiding the loss of precious tissue/cell samples from patients. In comparison, the common method for handling fungal contamination was to directly discard cells when fungal hyphae were observed under a microscope, which would cause waste of precious samples from patients.

Analysis of Washing Solution Mechanism

The mechanism of action for each component in the washing solution of the present application was as follows:

in the washing solution of the present application, the penicillin-streptomycin mixture added in the solution A effectively removed bacteria, while amphotericin B effectively removed fungi.

In the solution B, the volume fraction of penicillin-streptomycin was doubled compared to normal, and relevant results showed that this effectively inhibited microbial growth while having minimal impact on cell proliferation.

The penicillin-streptomycin stock solution in the solution C could rapidly eliminate microorganisms at high concentrations in a short time.

The trypsin solution in the solution D could rapidly digest cells in poor condition due to microbial infection at high concentrations in a short time, thus eliminating potential pathogens.

Through this multi-step washing method, the present application successfully solved the contamination problem in the microgravity cultivation of primary cancer cells, greatly improved the cultivation success rate, and provided an important guarantee for the effective utilization of precious tumor samples from patients.

Example 4: Digestion Solution Formulations and Digestion Methods

In establishing microgravity cultivation models of cancer cells derived from patients, the digestion treatment of tissues was a crucial step. Tissue blocks obtained from patient surgeries needed to be separated into single cell suspensions through effective digestion methods before subsequent cultivation could be performed. Selecting appropriate digestion solutions and optimizing digestion methods played a decisive role in obtaining sufficient quantities and good quality primary cancer cells.

Digestion Solution 1 #

A cancer cell digestion solution, comprising: 900 μL Collagenase/Hyaluronidase DMEM solution, 8100 μL of culture medium 1 # from Example 1, and 3 mL of dispase HBSS solution, wherein a concentration of dispase in HBSS was 5 U/mL.

Digestion Solution 2 #

A cancer cell digestion solution, comprising: 1000 μL Collagenase/Hyaluronidase DMEM solution, 7800 μL of culture medium 1 # from Example 1, and 2 mL of dispase HBSS solution, wherein a concentration of dispase in HBSS was 6 U/mL.

Digestion Solution 3 #

A cancer cell digestion solution, comprising: 800 μL Collagenase/Hyaluronidase DMEM solution, 8400 μL of culture medium 1 # from Example 1, and 5 mL of dispase HBSS solution, wherein a concentration of dispase in HBSS was 4 U/mL.

Digestion Method 1 #

A cancer cell digestion method, using digestion solution 1 #, comprising the following steps:

S1: pouring 80 mL of anhydrous ethanol into a 100 ml beaker, placing ophthalmic forceps and blades in the beaker, placing the beaker in a clean bench, and thoroughly sterilizing the ophthalmic forceps and blades;

S2: transferring the prepared digestion solution into 15 mL centrifuge tubes, 6 mL per tube;

S3: using the ophthalmic forceps to clamp tissue, placing the tissue in a 10 mL sterile culture dish, and subsequently cutting the tissue into millet-sized pieces using the blade;

S4: transferring the minced tissue mash into a centrifuge tube containing tissue digestion solution, clearly marking the tissue source, such as patient name, on the tube cap and tube body, tightening the tube cap, wrapping with sealing film, and placing on a 37° C. shaker at a speed of 220 rpm for 4 h to thoroughly digest the tissue. The digestion conditions could be fine-tuned, such as placing on a 37±1° C. shaker at a speed of 200~250 rpm for 3.5~4.5 h to thoroughly digest the tissue.

Comparative Digestion Method D1 #

This comparison was basically the same as digestion method 1 #, with the difference being a use of 0.25% trypsin on a 37° C. shaker at 220 rpm for 4 h digestion.

Comparative Digestion Method D2 #

This comparison was basically the same as digestion method 1 #, with the difference being a use of collagenase IV on a 37° C. shaker at 220 rpm for 4 h digestion.

Digestion Effect Comparison Experiment

Digestion method 1 # was the digestion method of the present application, while the comparative methods D1 # and D2 # are enzyme-based protocols commonly used in laboratories for isolating primary cancer tissues. The enzymes used and their application protocols differ from those of the present invention. To confirm the digestion effect of digestion method 1 #, the inventors digested cancer tissue from the same patient using the operation methods described in digestion method 1 # and comparative digestion methods D1 # and D2 #.

Figure 5:
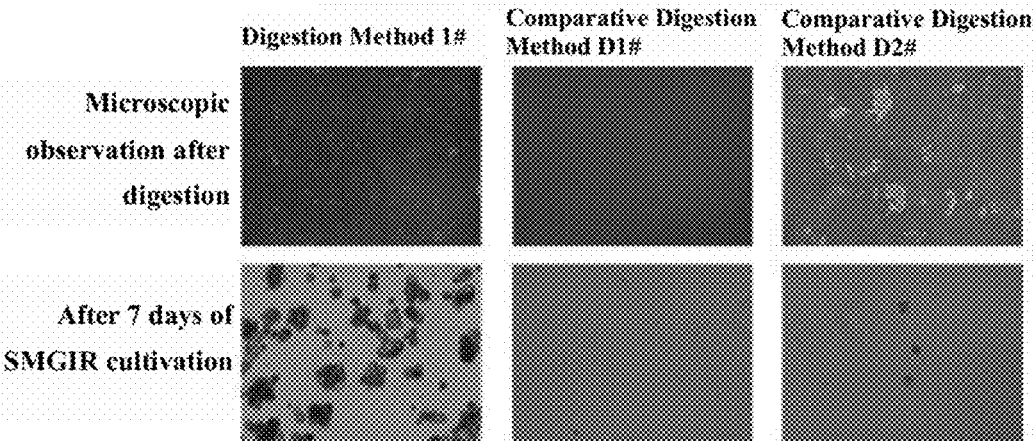
FIG. 5 shows the digestion and cell cultivation results of samples from the same breast cancer patient as related to the present application.

As shown in FIG. 5, according to the results, the digestion solution and digestion method of the present application had better digestion effects on tissues, yielding a considerable number of cells, while the enzymes and digestion methods described in comparative digestion methods D1 # and D2 # yielded fewer cells, making it impossible to expand a large number of cells in a microgravity environment.

Analysis of Differences in Digestion Effects

Trypsin is currently the most widely used cell/tissue digestion reagent, but it is suitable for digesting soft tissues with relatively little interstitial cells. Cancer tissues contain many interstitial cells, and most cancer tissues are relatively hard, which may be the reason why trypsin digestion did not produce a considerable number of cells.

Collagenase only had digestive effects on interstitial cells but minimal impact on epithelial cells, which resulted in epithelial cancer cells in cancer tissues not being digested down. Therefore, even with a relatively large initial number of cells, it was still impossible to expand cells in a microgravity environment.

In contrast, the digestion method provided by the present application combined the advantages of multiple enzymes. Collagenase/Hyaluronidase DMEM solution effectively decomposed collagen and hyaluronic acid, dispase could further digest connections between cells, and the culture medium provided in Example 2 provided nutritional support for cells during the digestion process. This combined digestion method could both ensure cell quantity and quality, making cancer cells maximally separated to facilitate growth and cultivation, while maintaining high cell viability. The cultivation effect was good, significantly improving the success rate of subsequent microgravity cultivation.

Through the optimization of the above digestion solutions and digestion methods, a reliable preliminary processing method was provided for the subsequent microgravity cultivation of various types of cancer cells, ensuring efficient conversion from tissue samples to single cell suspensions, and laying the foundation for establishing stable cancer cell models.

Example 5: Cultivation of Breast Cancer Cell Models

Based on the microgravity cultivation conditions, culture medium formulations, washing solutions, and digestion solutions optimized in Examples 1 to 4, this example describes in detail the establishment, cultivation, and performance verification process of breast cancer cell models.
1) Breast Cancer Patient Tissue Sampling and Pretreatment Breast cancer/cancer-adjacent tissues were obtained from the breast surgery department of medical institutions. Sample acquisition and use processes had received relevant clinical ethics approval. Breast cancer/cancer-adjacent tissues of approximately 1 mm$^3$ in volume were obtained during surgery, digested according to digestion method 1 # in Example 4 to obtain a single cell suspension. Then, according to the cell growth state, washing treatment was performed according to the washing method in Example 3. The obtained breast cancer/cancer-adjacent tissue single cell suspension was inoculated into a T25 culture flask and allowed to stand for 24 hours in a $CO_2$ cell incubator until the cells completely adhered to the wall.
2) Simulated Microgravity-Induced Reprogramming (SM-GIR) Cell Cultivation The T25 culture flask with adherent cells from the previous step was fixed on the rotating frame of the Gravite® gravity control system and placed entirely in a conventional $CO_2$ cell incubator for cultivation. The Gravite® gravity control system was set with an outer shaft rotation speed of maximum 8 rpm and minimum 6 rpm for the rotating frame, inner shaft rotation speed of maximum 5 rpm and minimum 3 rpm, controlling the microgravity environment within the range of $10^{-3}$ g with ±10% fluctuation, with a microgravity environment cultivation duration of 6.5~7.5 days.
3) Similarity Verification Between SMGIR Cells and Patient Original Tumor Tissues SMGIR cells and conditionally reprogrammed cells (CRC) of the 3rd, 6th, and 10th generations were collected separately. Whole exome sequencing was performed using the Illumina platform, and the results were compared with the sequencing results of the patient's original tumor tissue to analyze somatic mutations occurring during SMGIR and CRC cultivation.

Figure 6:
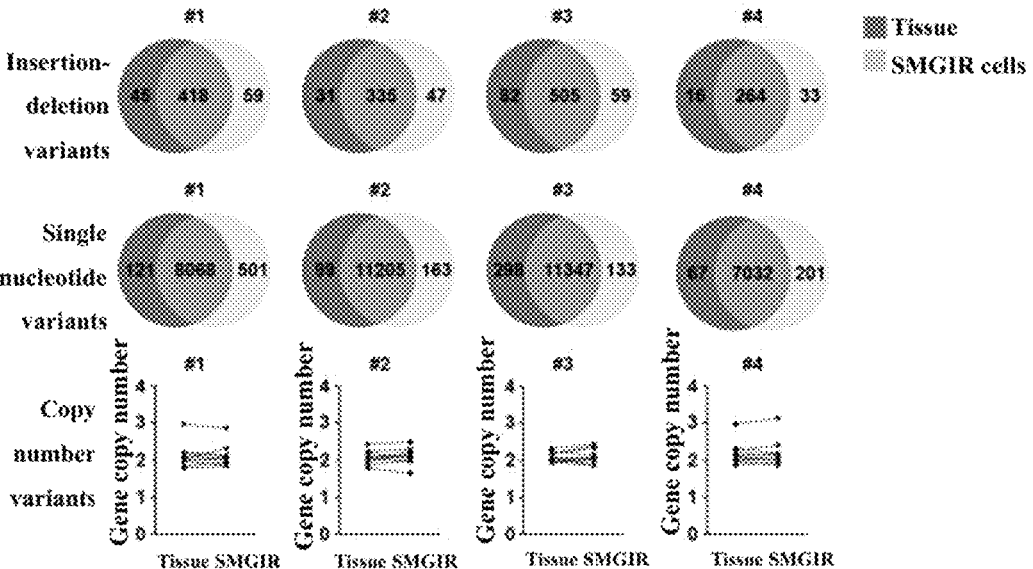
FIG. 6 shows the results of gene mutation conditions in SMGIR cultivation as related to the present application.

FIG. 6 shows the whole genome sequencing performed on original cancer tissues and SMGIR cells (3rd generation) from 4 breast cancer patients, analyzing insertion-deletion variants, single nucleotide variants, and copy number variants of key genes (BRCA1, BRCA2, PTEN, TP53, PIK3CA, CDH1, STK11, CCND1, MYC, RB1). The results showed that at the 3rd generation of cultivation, SMGIR cells maintained good consistency with the original cancer tissue in terms of gene mutations, demonstrating that the SMGIR cultivation process did not cause significant gene mutations in primary breast cancer cells.

4) SMGIR Cell Tumorigenicity Experiment

SMGIR cells were collected and inoculated into the mammary fat pads of immunodeficient mice. Tumor formation was checked regularly, and tumor size was recorded.

Figure 7A:
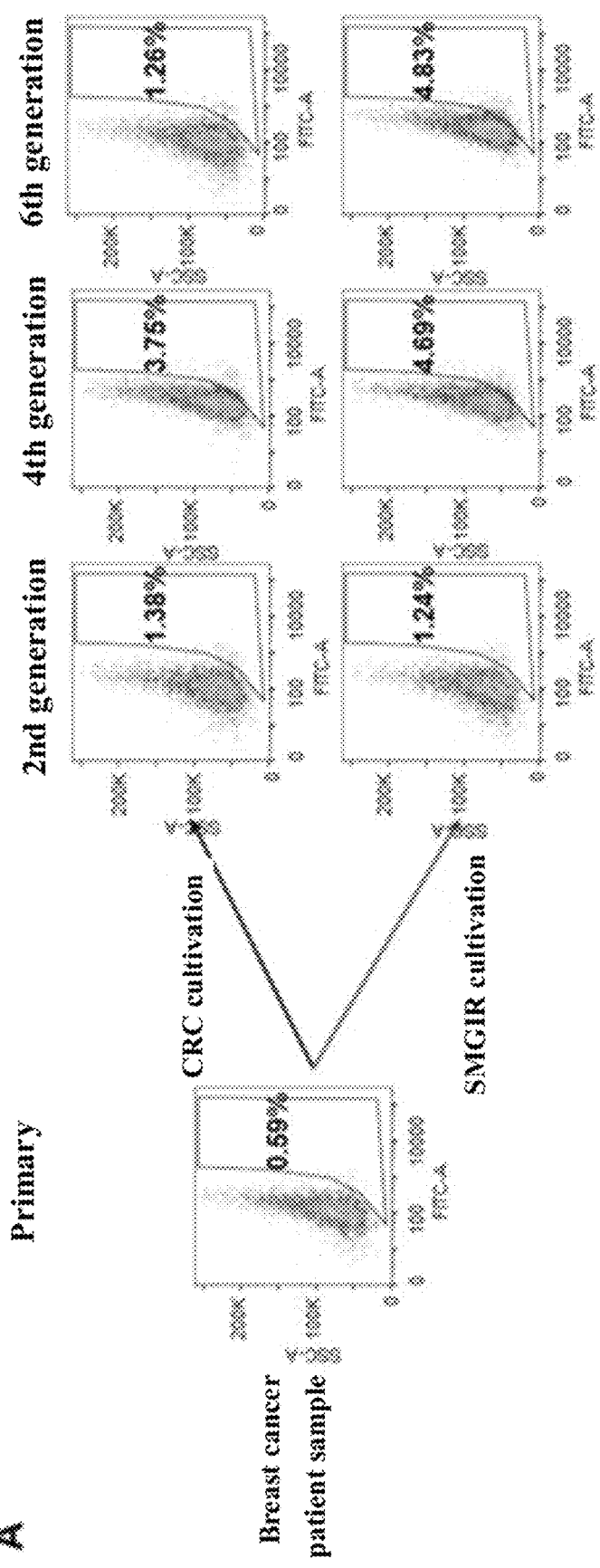
FIG. 7A shows flow cytometry analysis results for detecting the proportion of ALDH-positive cells (cancer stem cells) in breast cancer cells under different cultivation conditions and passage numbers. The figure displays the proportion of ALDH-positive cells in primary breast cancer tissue (primary) and under two different cultivation methods (CRC cultivation and SMGIR cultivation) at different passage numbers (2nd, 4th, and 6th generation).
Figures 7B, 7C:
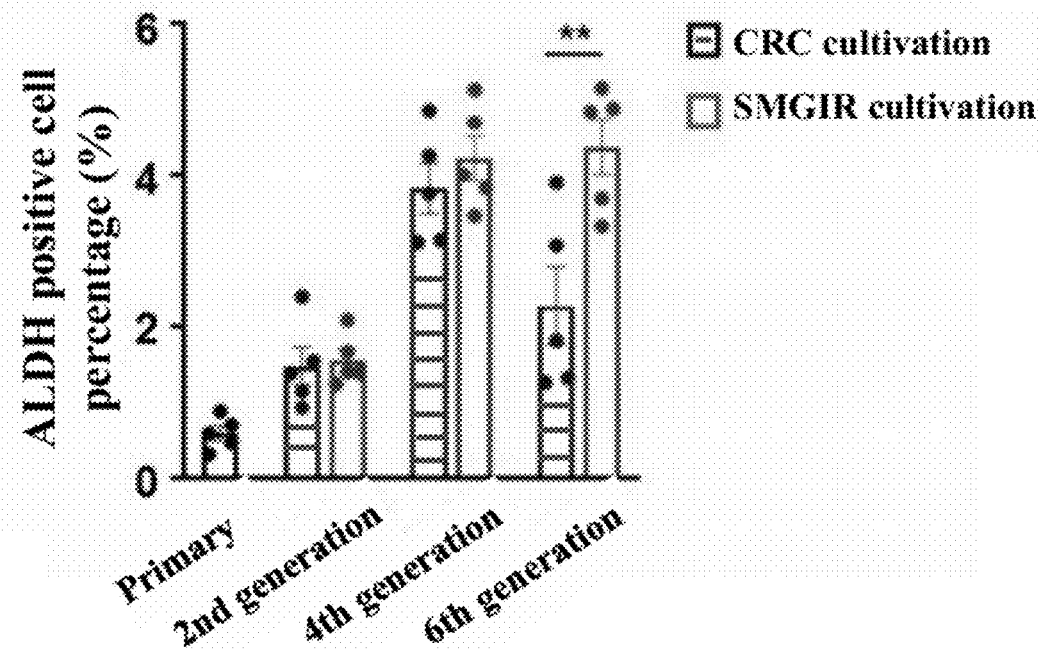
FIG. 7B is a statistical analysis result of FIG. 7A data, showing in bar graph form the quantitative comparison of ALDH-positive cell percentages under different cultivation methods (CRC cultivation and SMGIR cultivation) and generations.
FIG. 7C shows the results of in vivo tumorigenicity experiments of breast cancer cells cultured by CRC and SMGIR at different passage numbers.

The part of FIG. 7C shows statistics on tumor formation in mice 70 days after various generations of breast cancer cells cultivated by SMGIR were inoculated into mammary fat pads of immunodeficient mice. The results indicated that cells cultivated by SMGIR maintained good tumorigenicity, and although the tumor formation rate slightly decreased with increasing passage number, it generally remained at a high level.
5) SMGIR Cell Stemness Analysis Cells from the 2nd to 10th generations of SMGIR were collected separately. Through Aldefluor assay and mammosphere formation assay, the proportion of breast cancer stem cells in each generation of SMGIR was detected and compared with the proportion of breast cancer stem cells in the original tumor tissue from the same patient. Changes in breast cancer stem cells during the SMGIR cultivation process were monitored generation by generation.

Figure 8:
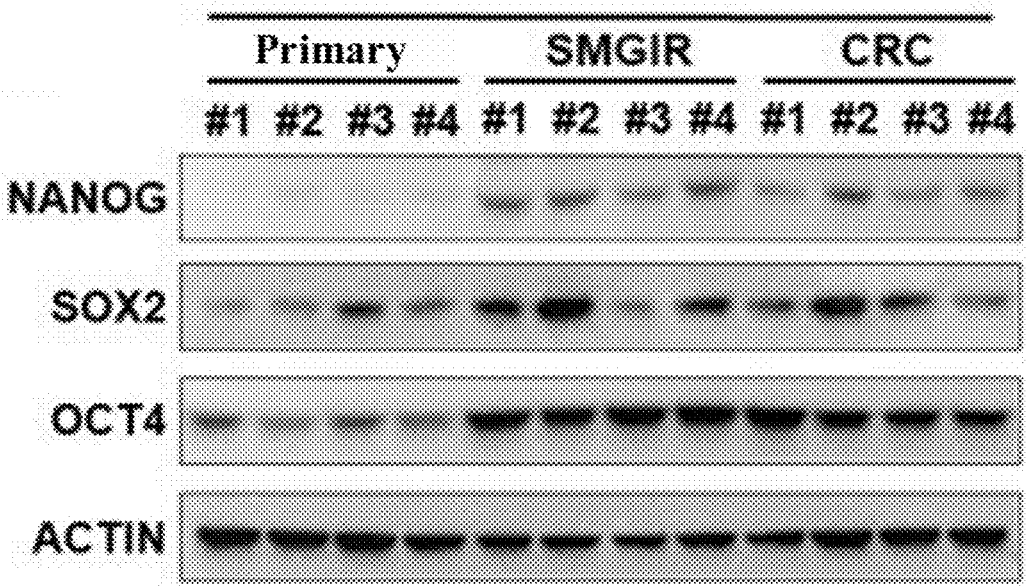
FIG. 8 shows the expression results of pluripotency factors in SMGIR cultured cells as related to the present application.
Figure 9A:
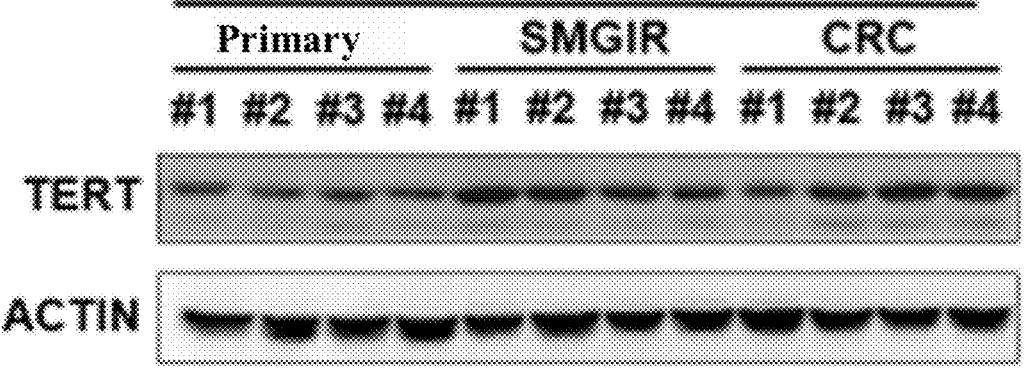
FIG. 9A shows Western blot experimental results for detecting telomerase reverse transcriptase (TERT) protein expression levels in different samples.
Figure 9B:
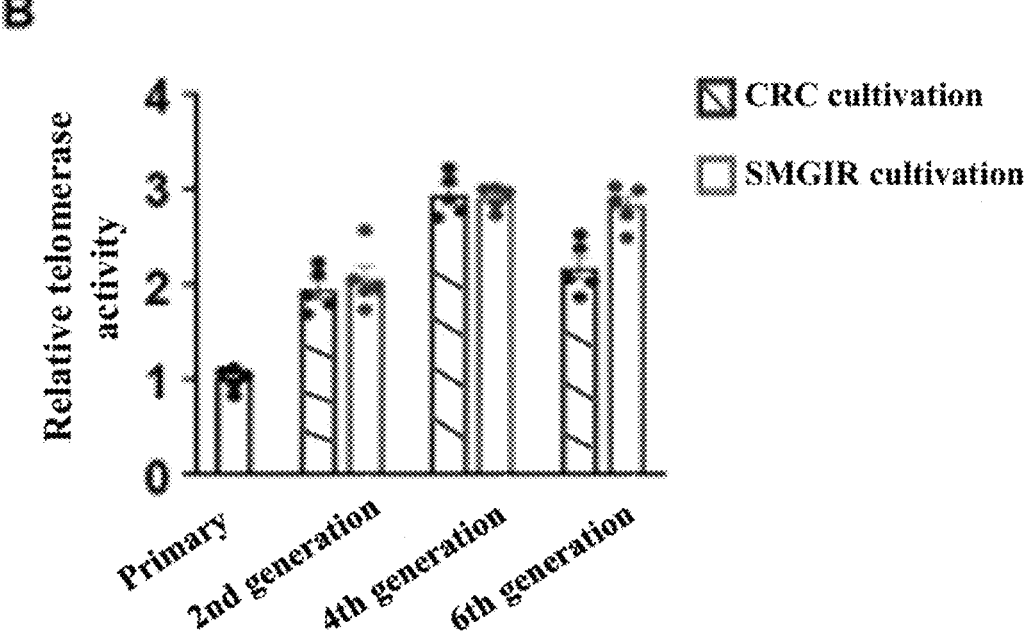
FIG. 9B shows quantitative comparison results of telomerase activity under different cultivation methods and generations.

FIGS. 7A and 7B show the cultivation of primary breast cancer cells from patients using CRC technology and SMGIR technology, respectively. In the 2nd, 4th, and 6th generations of cell cultivation, some cells were collected and stained for tumor stem cell marker aldehyde dehydrogenase (ALDH) activity, and the proportion of ALDH-positive cells was detected by flow cytometry. The results showed that with the induction of an increase in the proportion of tumor stem cells as an indicator, SMGIR technology could achieve effects similar to CRC technology cultivation without using mouse embryonic fibroblasts and ROCK inhibitors. It is worth noting that when primary breast cancer cells were cultivated to the 6th generation using CRC technology, the proportion of tumor stem cells had significantly decreased, but cultivation using SMGIR technology could still maintain a high proportion of tumor stem cells. FIG. 7A shows a representative image of flow cytometry detection of ALDH-positive cells in breast cancer patient samples, and FIG. 7B shows statistical results (n=5).
6) Effects of SMGIR Cultivation on the Expression of Cell Pluripotency Factors FIG. 8 shows the cultivation of primary breast cancer cells from patients using CRC technology and SMGIR technology, respectively. In the 5th generation of cell cultivation, some cells were collected, and cell pluripotency factor expression was detected using Western Blot. The results showed that compared with the original cancer tissue, SMGIR cultivation induced significant increases in the expression of cell pluripotency factors NANOG, SOX2, and OCT4. This indicated that the microgravity environment could effectively activate stemness-related pathways in cancer cells, promoting cell reprogramming.
7) Effects of SMGIR Cultivation on Cell Telomerase Activity FIG. 9A shows the cultivation of primary breast cancer cells from patients using CRC technology and SMGIR technology, respectively. In the 5th generation of cell cultivation, some cells were collected, and telomerase reverse transcriptase (TERT) expression was detected using Western Blot; FIG. 9B shows that in the 2nd, 4th, and 6th generations of cell cultivation, some cells were collected, and telomerase activity was detected using a telomerase activity detection kit (ScienCell). The results showed that compared with the original cancer tissue, SMGIR cultivation significantly increased TERT protein expression levels and telomerase activity. Increased telomerase activity helped cells maintain proliferation ability, prevent cell senescence, and was an important indicator of cells acquiring long-term in vitro cultivation ability.

8) Comparison of SMGIR Cultivation Results with CRC Technology

Figure 10:
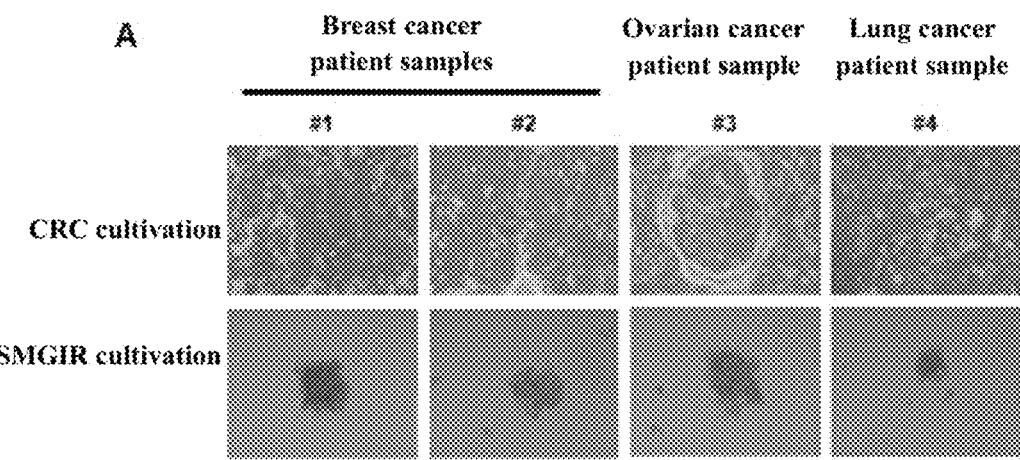
FIG. 10 shows the cultivation results of CRC and SMGIR techniques as related to the present application.

FIG. 10 shows the cultivation of primary breast cancer cells from patients using CRC technology (co-cultivation with mouse embryonic fibroblasts and addition of ROCK inhibitor) and SMGIR technology, respectively. The images shown are representative photos of breast cancer cells from 4 patients when cells were passaged to the 3rd generation. The results showed that simulated microgravity could replace mouse embryonic fibroblasts and ROCK inhibitors, induce reprogramming of primary breast cancer cells, and successfully achieve long-term in vitro cultivation of primary breast cancer cells.

Through the above verification experiments, it was demonstrated that the SMGIR method of the present application could successfully establish stable breast cancer cell models. These models maintained high consistency with the patient's original tumor tissue, while possessing good stem cell characteristics and proliferation ability, providing reliable cell models for subsequent drug screening and mechanism research.

Example 6: Cultivation of Ovarian Cancer Cell Models

Based on the microgravity cultivation conditions, culture medium formulations, washing solutions, and digestion solutions optimized in Examples 1 to 4, this example describes in detail the establishment and cultivation process of ovarian cancer cell models. Due to the special nature of the ovarian cancer surgical process and the characteristics of its tissue source environment, ovarian cancer samples were typically more susceptible to contamination than breast cancer samples, therefore requiring special attention to washing and decontamination steps during processing.

1) Ovarian Cancer Patient Tissue Sampling and Pretreatment

Ovarian cancer/cancer-adjacent tissues were obtained from the gynecology department of medical institutions. Sample acquisition and use processes had received relevant clinical ethics approval. Ovarian cancer/cancer-adjacent tissues of approximately 1 mm³ in volume were obtained during surgery and digested according to digestion method 1 # in Example 4. After being digested into a single cell suspension and centrifuged, the tissue digestion solution was discarded, and cells were thoroughly washed by pipette trituration using the solution A from washing solution 1 # in Example 3. After centrifugation, the solution A was discarded, and cells were resuspended in the solution B from washing solution 1 #, and allowed to stand for 24 hours in a $CO_2$ cell incubator until the cells completely adhered to the wall.

2) Contamination Detection and Decontamination Treatment

The next day, if the culture medium was turbid but no obvious fungal hyphae were present: the solution B in the flask was aspirated and discarded; cells were thoroughly washed by pipette trituration using the solution A; the solution A was aspirated and discarded; the above operations were repeated 2~4 times, then cultivation was continued using the solution B.

If the culture medium was turbid and obvious fungal hyphae were present: the solution B in the flask was aspirated and discarded; cells were thoroughly washed by pipette trituration using the solution A; the solution A was aspirated and discarded; cells were thoroughly washed by pipette trituration using the solution C from washing solution 1 # in Example 3; the solution C was aspirated and discarded; cells were thoroughly washed by pipette trituration using the solution D from washing solution 1 # in Example 3 for 1~3 min; the solution D was aspirated and discarded; cells were thoroughly washed by pipette trituration using the solution A; the solution A was aspirated and discarded; the above operations were repeated 2~4 times, then cultivation was continued using the solution B.

Daily observation and repetition of the above operations were performed until the cells recovered to a normal sterile state after three days, then routine cultivation was conducted using culture medium.

3) Simulated Microgravity-Induced Reprogramming (SMGIR) Cultivation

The T25 culture flask of ovarian cancer cells treated through the above steps was fixed on the rotating frame of the Gravite® gravity control system and cultivated according to the microgravity cultivation conditions determined in Example 1 (outer shaft rotation speed of the rotating frame set to maximum 8 rpm and minimum 6 rpm, inner shaft rotation speed set to maximum 5 rpm and minimum 3 rpm, controlling the microgravity environment within the range of $10^{-3}$ g with ±10% fluctuation), with a cultivation duration of 6.5~7.5 days.

4) Ovarian Cancer SMGIR Cultivation Results

SMGIR successfully cultivated primary ovarian cancer cells derived from patients. FIG. 10 shows the cultivation of primary ovarian cancer cells from patients using CRC technology (co-cultivation with mouse embryonic fibroblasts and addition of ROCK inhibitor) and SMGIR technology, respectively. The images shown are representative photos of ovarian cancer cells from one patient when cells were passaged to the 3rd generation. The results showed that simulated microgravity could replace mouse embryonic fibroblasts and ROCK inhibitors, induce reprogramming of primary ovarian cancer cells, and successfully achieve long-term in vitro cultivation of primary ovarian cancer cells.

As shown in FIG. 10, ovarian cancer cell samples (#3) cultivated using the SMGIR method could form obvious spherical structures, similar to breast cancer cells cultivated using the same method. In contrast, ovarian cancer cells cultivated using CRC technology exhibited adherent growth.

Through this example, it was demonstrated that the SMGIR method was not only applicable to breast cancer cells but also to the long-term cultivation of ovarian cancer cells. Particularly in solving the problem of easy contamination of ovarian cancer tissues, the washing method provided by the present application could effectively preserve precious patient samples, showing significant advantages. This provided a unified technology platform for establishing various types of cancer cell models.

Example 7: Cultivation of Lung Cancer Cell Models

Based on the microgravity cultivation conditions, culture medium formulations, washing solutions, and digestion solutions optimized in Examples 1 to 4, this example describes in detail the establishment and cultivation process of lung cancer cell models. Due to the special nature of lung cancer tissues and potential contamination risks during clinical sample acquisition, this example focuses on the processing and cultivation characteristics of lung cancer cells.

1) Lung Cancer Patient Tissue Sampling and Pretreatment

Lung cancer/cancer-adjacent tissues were obtained from medical institutions. Sample acquisition and use processes had received relevant clinical ethics approval. Lung cancer/cancer-adjacent tissues of approximately 1 mm³ in volume were obtained during surgery and digested according to digestion method 1 # in Example 4. After being digested into a single cell suspension and centrifuged, the tissue digestion solution was discarded, and cells were thoroughly washed by pipette trituration using the solution A from washing solution 1 # in Example 3. After centrifugation, the solution A was discarded, and cells were resuspended in the solution B from washing solution 1 #, and allowed to stand for 24 hours in a $CO_2$ cell incubator until the cells completely adhered to the wall.

2) Contamination Detection and Decontamination Treatment

The next day, if the culture medium was turbid but no obvious fungal hyphae were present: the solution B in the flask was aspirated and discarded; cells were thoroughly washed by pipette trituration using the solution A; the solution A was aspirated and discarded; the above operations were repeated 2~4 times, then cultivation was continued using the solution B.

If the culture medium was turbid and obvious fungal hyphae were present: the solution B in the flask was aspirated and discarded; cells were thoroughly washed by pipette trituration using the solution A; the solution A was aspirated and discarded; cells were thoroughly washed by pipette trituration using the solution C from washing solution 1 # in Example 3; the solution C was aspirated and discarded; cells were thoroughly washed by pipette trituration using the solution D from washing solution 1 # in Example 3 for 1~3 min; the solution D was aspirated and discarded; cells were thoroughly washed by pipette trituration using the solution A; the solution A was aspirated and discarded; the above operations were repeated 2~4 times, then cultivation was continued using the solution B.

Daily observation and repetition of the above operations were performed until the cells recovered to a normal sterile state after three days, then routine cultivation was conducted using culture medium.

3) Simulated Microgravity-Induced Reprogramming (SMGIR) Cultivation

The T25 culture flask of lung cancer cells treated through the above steps was fixed on the rotating frame of the Gravite® gravity control system and cultivated according to the microgravity cultivation conditions determined in Example 1 (outer shaft rotation speed of the rotating frame set to maximum 8 rpm and minimum 6 rpm, inner shaft rotation speed set to maximum 5 rpm and minimum 3 rpm, controlling the microgravity environment within the range of $10^{-3}$ g with ±10% fluctuation), with a microgravity environment cultivation duration of 6.5~7.5 days.

4) Lung Cancer SMGIR Cultivation Results

SMGIR successfully cultivated primary lung cancer cells derived from patients. FIG. 10 shows the cultivation of primary lung cancer cells from patients using CRC technology (co-cultivation with mouse embryonic fibroblasts and addition of ROCK inhibitor) and SMGIR technology, respectively. The images shown are representative photos of lung cancer cells from one patient when cells were passaged to the 3rd generation. The results showed that simulated microgravity could replace mouse embryonic fibroblasts and ROCK inhibitors, induce reprogramming of primary lung cancer cells, and successfully achieve long-term in vitro cultivation of primary lung cancer cells.

As shown in FIG. 10, lung cancer cell samples (#4) cultivated using the SMGIR method could form obvious spherical structures, similar to breast cancer and ovarian cancer cells cultivated using the same method. In contrast, lung cancer cells cultivated using CRC technology exhibited adherent growth. This result demonstrated that the SMGIR method was not only applicable to the cultivation of breast cancer and ovarian cancer cells but also to the cultivation of lung cancer cells.

Through the results of this example, the effectiveness of the SMGIR method in the cultivation of primary lung cancer cells was further verified, expanding the application range of this technology in the cultivation of different types of cancer cells. Due to the environmental influence of lung cancer cell/tissue growth and operational influences during surgery, the obtained lung cancer cell/tissues were also very susceptible to contamination. Therefore, extra attention needed to be paid to the washing steps in the processing of lung cancer cells/tissues. The washing method provided by the present application was of significant importance for preserving precious lung cancer patient samples. This provided a new technical approach for establishing lung cancer cell models, which was of great significance for basic research and drug screening for lung cancer.

Example 8: Testing the Repeated Cultivation Ability of Cell Models

This example aimed to evaluate the repeated cultivation ability of cancer cell models cultivated using the SMGIR method, to verify whether cell models obtained by this method could withstand cryopreservation and resuscitation operations while maintaining stable proliferation ability, meeting the needs of clinical research and drug screening.

1) Testing the Cultivation Ability of Cancer Cell Models Established from Fresh Tissues As shown in the left panel of FIG. 11, using the method of the present application to cultivate fresh breast cancer tissue that had been removed from the body within 8 hours after surgery, the cell number could reach approximately $10^6$ cells after 7 days of cultivation in a microgravity environment. This indicated that the SMGIR method could effectively establish stable cell models from fresh cancer tissues and obtain sufficient numbers of cells for subsequent experiments in a short period of time.

2) Testing the Cultivation Ability after Resuscitation of Cryopreserved Tissues

As shown in the middle panel of FIG. 11, the inventors resuscitated, digested, and cultivated the tissue samples from the same breast cancer patient that had been obtained and cryopreserved six months earlier. The results showed that after 7 days of SMGIR cultivation following the resuscitation of cryopreserved tissues, the total number of cells obtained showed no significant difference from that obtained from fresh tissue cultivation. This result demonstrated that the SMGIR method was applicable not only to the cultivation of fresh tissues but also to tissue samples that had been cryopreserved, which was of great significance for establishing biobanks of cancer patient samples.

3) Testing the Cultivation Ability after Cryopreservation of Passaged Cells

As shown in the right panel of FIG. 11, the inventors cryopreserved cells that had already undergone SMGIR cultivation and passaging, and after resuscitation, cultivated them again using the SMGIR method for 7 days. The results showed that although the total number of cells was less than the previous two groups, 750,000-1,000,000 cells could still be obtained after 7 days, indicating that cancer cells cultivated using the SMGIR method could maintain good proliferation ability even after passaging and cryopreservation.

The above results indicated that the tumor cell model cultivation method provided by the present application could enable tumor cell models to undergo repeated cultivation, thereby meeting the needs for drug testing on tumor cells or other requirements in clinical settings.

4) Comparison with Existing Technologies

In existing technologies, such as the published articles "Cancer cell lines for drug discovery and development" (Wilding, J. L. & Bodmer, W. F. Cancer Res. 74, 2377-2384 (2014)) and "The two-stage mechanism controlling cellular senescence and immortalization" (Wright, W. E. & Shay, J. W. Exp. Gerontol. 27, 383-389 (1992)), primary cultivation was directly performed on most post-surgical patient tumor blocks. However, regardless of the method used to cultivate them, they were difficult to maintain because they had limited lifespans, gradually reduced proliferation, and eventually led to senescence.

In contrast, the method provided by the present application successfully prepared cancer cell tumor models. For example, through 7 days of cultivation, the cell number could reach the level of millions, and as a cell model, it had the characteristic of being able to be repeatedly utilized for cultivation. Using these cultivated cells and applying the microgravity environment cultivation method of the present application, millions of tumor cells could still be obtained after 7 days. Therefore, long-term in vitro proliferation of cells derived from patients could be achieved, meeting usage needs.

5) Comparison with Other Tumor Model Methods

Although PDX models could well cultivate primary cells derived from patients in vitro, because PDX was established through subcutaneous xenografts in mice, the normal tissue counterparts and surrounding interacting stroma of each patient were missing. Additionally, the PDX models were expensive, difficult to develop, and not suitable for high-throughput platforms. Furthermore, the success rate of this model was relatively low, only 30-50%.

In contrast, the present method could successfully cultivate cancer-adjacent cells in vitro as controls for cancer cells, thereby effectively evaluating drug safety. Moreover, this method was suitable for high-throughput drug screening and could directly use 96-well plates/384-well plates for drug screening, with a success rate also far higher than that of the PDX models.

Organoids were a type of 3D culture derived from patient cells, and this model could support the growth of normal tissues and cancer tissues, but it was not easily adaptable to high-throughput screening. In contrast, the present method was suitable for high-throughput drug screening and could directly use 96-well plates/384-well plates for drug screening, with more convenient and reliable result reading.

Through the results of this example, it was demonstrated that cancer cell models obtained by the SMGIR method possessed good repeated cultivation ability and stability, and could support the establishment of long-term stable cell models from relatively small amounts of patient tissue samples, providing reliable cell sources for cancer research and drug screening.

Example 9: Drug Effect Testing

This example aimed to verify the application value of cancer cell models obtained through the SMGIR method in drug screening, exploring whether they could accurately reflect the differential responses of different patients and different cell types to drugs, providing experimental basis for precision treatment of cancer.

1) Drug Screening Experiment Design

Figures 12B, 12C:
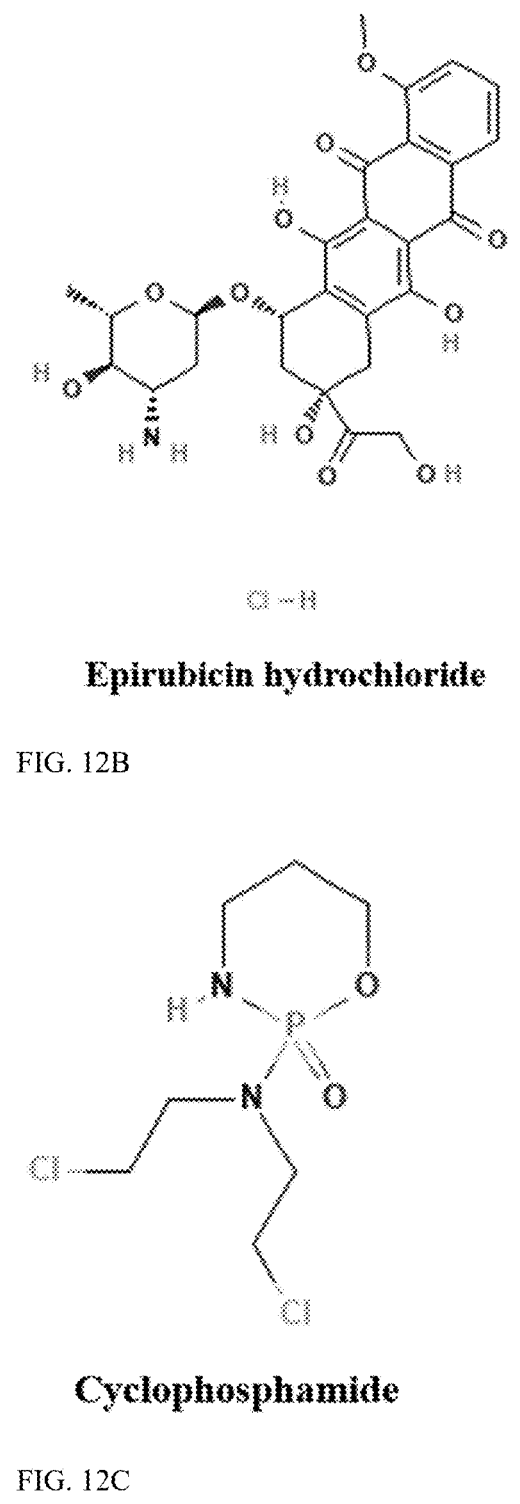
Figure 12D:
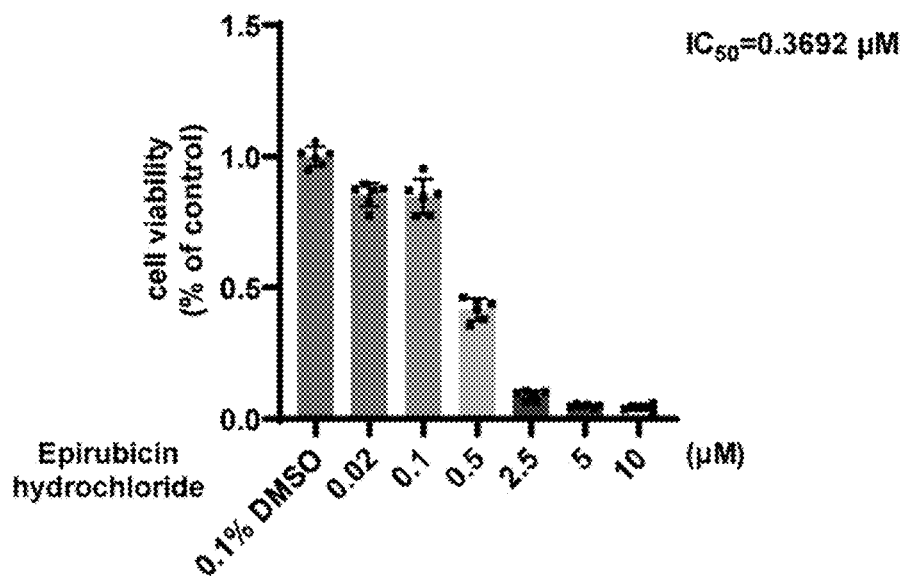
Figure 12E:
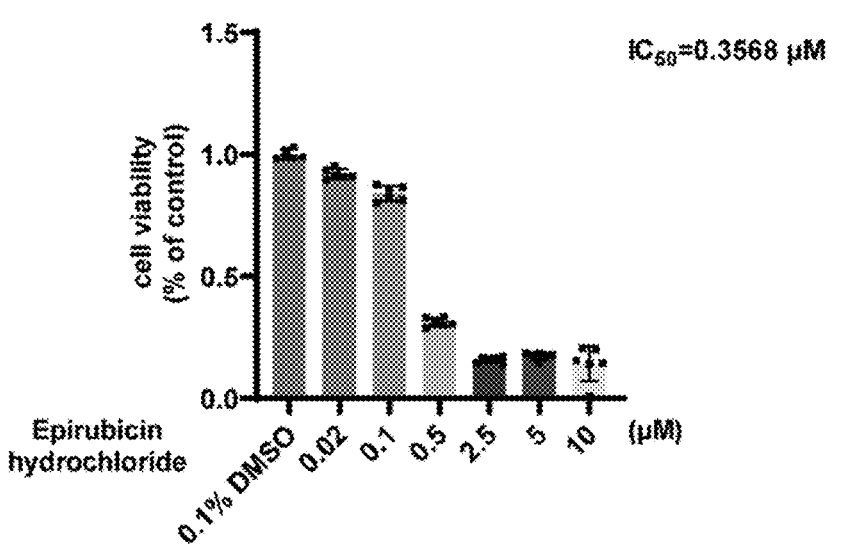
Figure 12F:
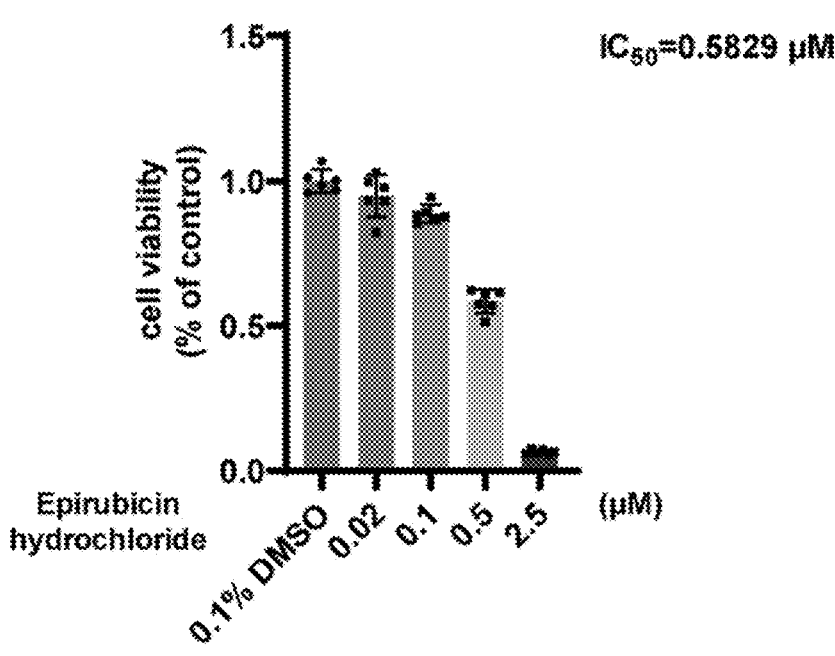
Figure 12G:
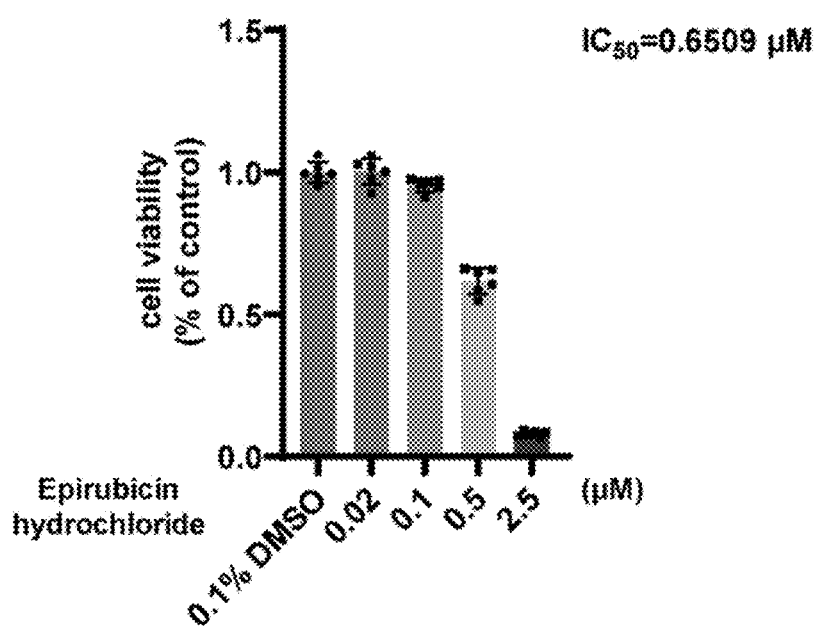
Figure 12H:
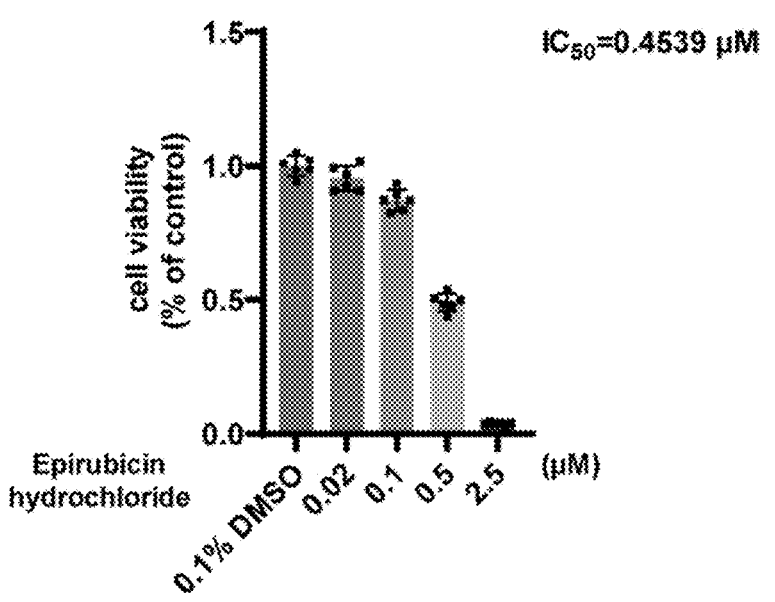
Figure 12I:
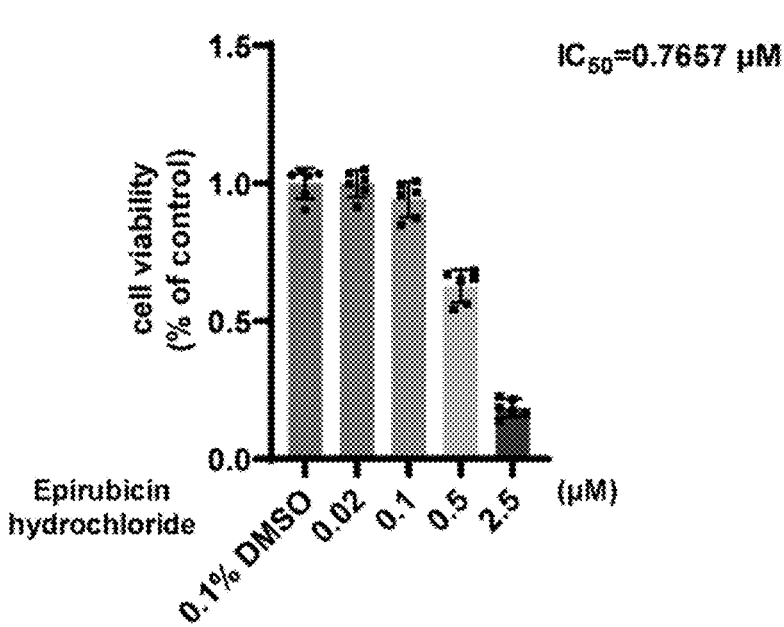
Figure 12J:
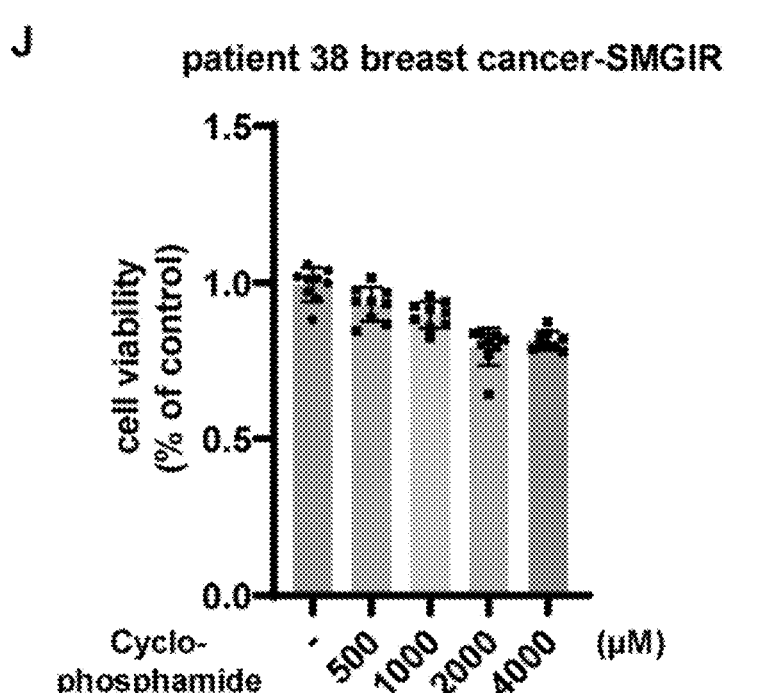
Figure 12K:
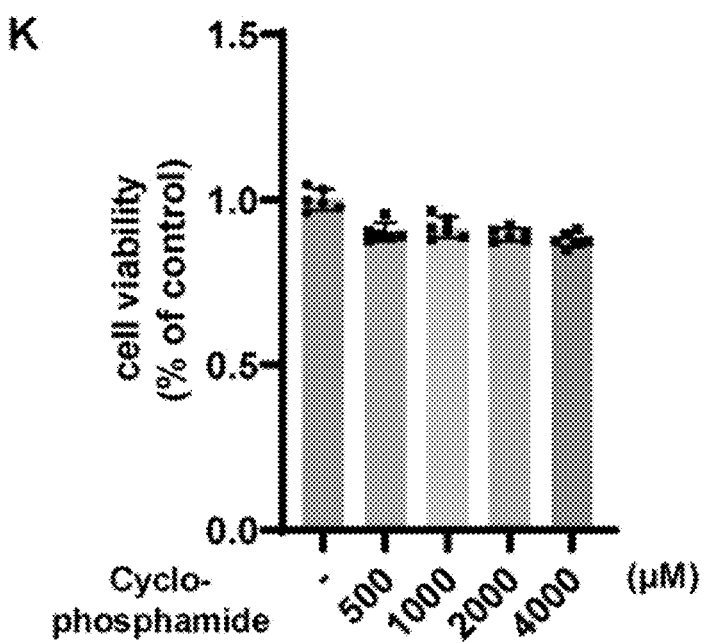
Figure 12L:
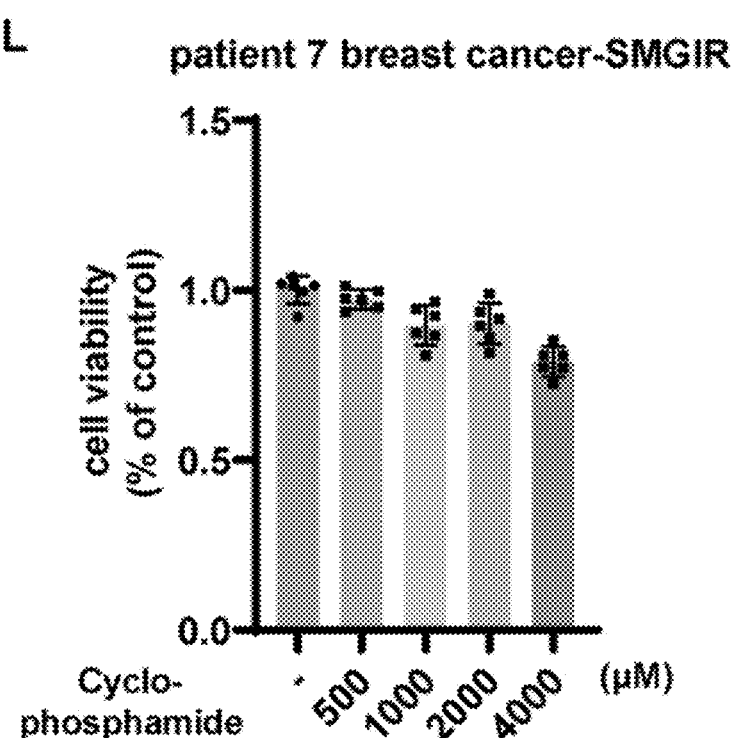
Figure 12M:
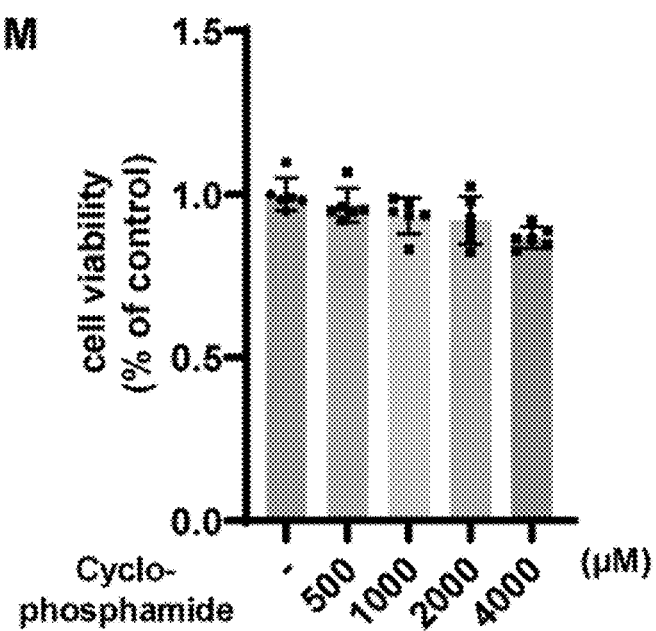
Figure 12N:
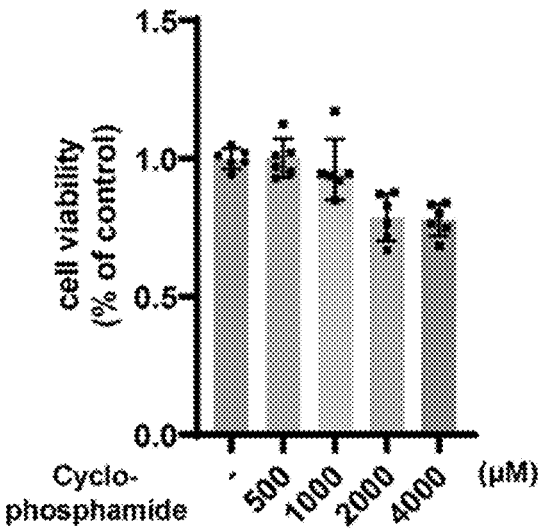
Figure 12O:
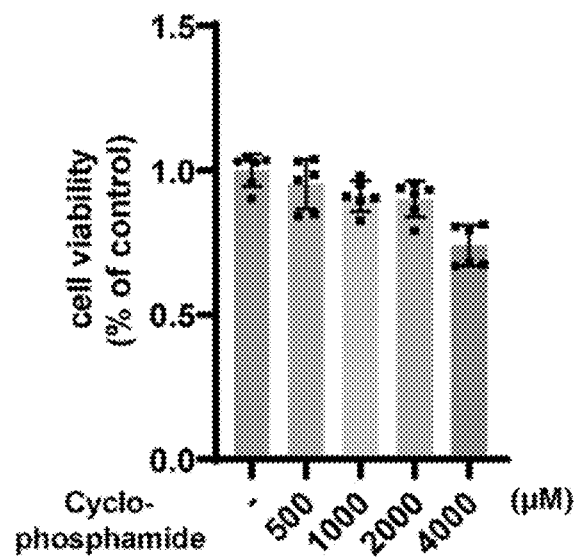

The inventors conducted drug-related experiments using the cancer cell models prepared by the method of the present application. FIG. 12A lists 8 types of common drugs used in clinical treatment of breast cancer, including epirubicin, cyclophosphamide, docetaxel, etc. This example selected two of them (FIG. 12B: epirubicin, FIG. 12C: cyclophosphamide) to conduct drug sensitivity tests on breast cancer cells from different patients cultivated in Example 5.

2) Drug Sensitivity Test Results

Using the cancer cell models constructed by the present application, the inventors were able to conduct drug administration experiments and evaluations, providing clinical basis for patient treatment. As shown in FIG. 12D to FIG. 12O, the inventors tested epirubicin and cyclophosphamide and found significant differences in $IC_{50}$ values among different patients responding to the same drug. Additionally, there were also differences in response levels between cancer cells and cancer-adjacent cells from the same patient to the same drug.

Specifically, the epirubicin test results (FIG. 12D-I) showed that the $IC_{50}$ values of breast cancer cells from patients 38, 7, and 71 were 0.3692 μM, 0.5829 μM, and 0.4539 μM, respectively, with the difference between the most sensitive and least sensitive patients reaching twofold. The $IC_{50}$ values of normal breast tissue cells from the corresponding patients were 0.3568 μM, 0.6509 μM, and 0.7657 μM, indicating that epirubicin had a certain selective inhibitory effect on cancer cells. The cyclophosphamide test results (FIG. 12J-O) showed that in the high concentration range (500-4000 μM), cyclophosphamide had limited inhibitory effects on all samples, with most samples maintaining approximately 70-80% cell viability at the highest dose. This suggested that cyclophosphamide might not be the optimal treatment choice for these specific patients.

3) Clinical Significance of Drug Screening

Based on the above results, it could be clearly understood that in clinical treatment, precise drug administration should be targeted to different cancer cells and specific situations of different patients, which could both reduce treatment side effects and improve treatment effectiveness. For example, for patients highly sensitive to epirubicin, lower dose treatment regimens could be considered to reduce side effects; while for patients insensitive to this drug, alternative treatment drugs or adjusted treatment strategies might need to be considered.

Particularly noteworthy was that by simultaneously testing the responses of a patient's cancer cells and cancer-adjacent tissue cells to drugs, the therapeutic window of the drug could be assessed, i.e., the dose range in which the drug was effective against cancer cells but had minimal impact on normal tissue cells. This was of great significance for optimizing treatment regimens and reducing toxic side effects.

4) Advantages of SMGIR Cell Models in Drug Screening

The SMGIR cell models provided by the present application exhibited several obvious advantages in drug screening: they could maintain the genetic characteristics and drug response properties of the patient's original tissue; they could simultaneously cultivate cancer cells and cancer-adjacent cells, providing more comprehensive drug evaluation; they had a short cultivation cycle (sufficient numbers of cells could be obtained in 7 days); they were suitable for high-throughput screening platforms; and they possessed good stability and reproducibility.

These characteristics made SMGIR cell models ideal tools for drug screening in individualized cancer treatment, capable of providing more accurate drug sensitivity information for clinical treatment decisions, guiding clinicians in formulating individualized treatment plans.

The results of this example indicated that the cancer cell model construction method provided by the present application had important application value and significance for precision treatment of tumors. By rapidly screening the sensitivity of patient cancer cells to different drugs in vitro, the "trial and error" process in clinical practice could be avoided, improving the precision and effectiveness of treatment while reducing patients' economic burden and unnecessary toxic side effects, providing important support for precision medicine in cancer.

All of the above descriptions are merely embodiments of the present application, and the scope of protection of the present application is not limited by these specific embodiments, but is determined by the claims of the present application. For those skilled in the art, the present application can have various changes and variations. Any modifications, equivalent substitutions, improvements, etc., made within the technical ideas and principles of the present application should be included within the scope of protection of the present application.

The invention claimed is:

1. A method for simulated microgravity-induced reprogramming of primary cancer cells, comprising: obtaining cancerous tissue from a patient with cancer, digesting the cancerous tissue with a digestion solution and washing the cancerous tissue with washing solutions to obtain cancer cells for cultivation, cultivating the cancer cells in a culture medium using a multi-directional G-force generator to simulate a space microgravity environment, wherein the microgravity environment is $10^{-3}$ g with a fluctuation range of plus or minus 10%, wherein a cultivation duration in the microgravity environment is 6.5-7.5 days; wherein the culture medium used in the method comprises: 310-350 ml Dulbecco's Modified Eagle Medium (DMEM), 100-120 ml Ham's F12 nutrient mixture, 40-60 ml fetal bovine serum (FBS), 4-6 ml 200 mM glutamine solution, 4-6 ml penicillin-streptomycin mixture with penicillin at a concentration of 10 kU/ml and streptomycin at a concentration of 10 mg/ml, 400-600 μL hydrocortisone/epidermal growth factor (EGF) solution, 240-260 μL 10 mg/ml insulin, 4-6 μL 25 mg/ml amphotericin B, 90-110 μL 50 mg/ml gentamicin, 0.5-1.5 μL 5 mg/ml cholera toxin, and 480-520 μL 10 mM Y-27632; wherein hydrocortisone/ EGF solution is prepared by combining 25 μL of 0.1 mg/ml EGF solution with 19 ml of DMEM and 1 ml of 0.5 mg/ml hydrocortisone; wherein the cancer is breast cancer;

wherein the washing solutions used for washing comprise solution A, solution B, solution C, and solution D, wherein the solution A comprises: 400-600 ml phosphate-buffered saline (PBS), 4-6 ml penicillin-streptomycin mixture with penicillin at a concentration of 10 kU/ml and streptomycin at a concentration of 10 mg/ml, and 4-6 μl 25 mg/ml amphotericin B; the solution B comprises: 400-600 ml of the aforementioned culture medium and 8-12 ml penicillin-streptomycin mixture with penicillin at a concentration of 10 kU/ml and streptomycin at a concentration of 10 mg/ml; the solution C is penicillin-streptomycin mixture with penicillin at a concentration of 10 kU/ml and streptomycin at a concentration of 10 mg/ml; and the solution D is 0.04-0.06 wt % trypsin solution.

2. The method for simulated microgravity-induced reprogramming of primary cancer cells according to claim 1, wherein the method employs a gravity control system, and wherein the gravity control system is configured with an outer shaft rotation speed of maximum 8 rpm and minimum 6 rpm for a rotating frame, and an inner shaft rotation speed of maximum 5 rpm and minimum 3 rpm.

3. The method for simulated microgravity-induced reprogramming of primary cancer cells according to claim 1, wherein the washing comprises the following steps:

S1: centrifuging a tumor tissue sample after digestion, discarding a resulting tissue digestion solution, thoroughly washing resulting cells using the solution A; centrifuging and discarding the solution A; resuspending the cells in the solution B and culturing;

S2: observing the next day, if the culture medium is turbid but no obvious fungal hyphae are present: aspirating and discarding the solution B from flask; thoroughly washing cells by pipette trituration using the solution A; aspirating and discarding the solution A; repeating the above operations 2-4 times, then continuing cultivation using the solution B; if the culture medium is turbid and obvious fungal hyphae are present: aspirating and discarding the solution B from flask; thoroughly washing cells by pipette trituration using the solution A; aspirating and discarding the solution A;

thoroughly washing cells by pipette trituration using the solution C; aspirating and discarding the solution C;

thoroughly washing cells by pipette trituration using the solution D for 1-3 min; aspirating and discarding the solution D;

thoroughly washing cells by pipette trituration using the solution A; aspirating and discarding the solution A; repeating the above operations 2-4 times, then continuing cultivation using the solution B;

S3: observing daily and repeating the above S2 operation, until the cells recover to a sterile state after three days, then using the culture medium for cultivation.

4. The method for simulated microgravity-induced reprogramming of primary cancer cells according to claim 1, wherein a digestion solution used for digestion comprises: 800-1000 μL Collagenase/Hyaluronidase DMEM solution prepared from a 10× Collagenase/hyaluronidase in DMEM, 7800-8400 μL of the aforementioned culture medium, and 2-5 ml of Hank's Balanced Salt Solution (HBSS) solution of dispase, wherein a concentration of the dispase in HBSS is 4-6 U/ml.

5. The method for simulated microgravity-induced reprogramming of primary cancer cells according to claim 1, further comprising obtaining cancer-adjacent tissue from the same patient, and washing the cancer-adjacent tissue with the washing solutions to obtain cancer-adjacent cells for cultivation.

* * * * *